United States Patent
Freeman et al.

(10) Patent No.: US 11,324,443 B2
(45) Date of Patent: May 10, 2022

(54) AMPLITUDE SPECTRUM AREA CONSIDERATIONS FOR AN EXTERNAL MEDICAL MONITORING AND TREATMENT DEVICE

(71) Applicant: ZOLL Medical Corporation, Chelmsford, MA (US)

(72) Inventors: Gary A. Freeman, Waltham, MA (US); Christopher Luke Kaufman, Somerville, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 416 days.

(21) Appl. No.: 15/560,598

(22) PCT Filed: Mar. 24, 2016

(86) PCT No.: PCT/US2016/023992
§ 371 (c)(1),
(2) Date: Sep. 22, 2017

(87) PCT Pub. No.: WO2016/154425
PCT Pub. Date: Sep. 29, 2016

(65) Prior Publication Data
US 2018/0055442 A1    Mar. 1, 2018

Related U.S. Application Data

(60) Provisional application No. 62/138,680, filed on Mar. 26, 2015.

(51) Int. Cl.
*A61B 5/00* (2006.01)
*A61B 5/11* (2006.01)
(Continued)

(52) U.S. Cl.
CPC .......... *A61B 5/4836* (2013.01); *A61B 5/1118* (2013.01); *A61B 5/361* (2021.01);
(Continued)

(58) Field of Classification Search
CPC ... A61B 5/4836; A61B 5/7257; A61B 5/1118; A61B 2562/17; A61B 5/0205;
(Continued)

(56) References Cited

U.S. PATENT DOCUMENTS 5,046,504 A * 9/1991 Albert ................ A61B 5/04525
600/509
5,077,667 A 12/1991 Brown et al.
(Continued)

FOREIGN PATENT DOCUMENTS

| JP | 2005-339533 | 12/2005 |
|----|-------------|---------|
| JP | 2015-527097 | 9/2015 |

(Continued)

OTHER PUBLICATIONS

International Search Report and Written Opinion dated Jun. 10, 2016 in international application No. PCT/US2016/023992, 12 pgs.
(Continued)

*Primary Examiner* — Gary Jackson
*Assistant Examiner* — Sebastian X Lukjan
(74) *Attorney, Agent, or Firm* — ZOLL Medical Corporation

(57) ABSTRACT

A medical monitoring and treatment device that includes a therapy delivery interface, a plurality of therapy electrodes coupled to the therapy delivery interface, a plurality of electrocardiogram sensing electrodes to sense electrocardiogram signals of a patient, a sensor interface to receive the electrocardiogram signals and digitize the electrocardiogram signals, and at least one processor coupled to the sensor interface and the therapy delivery interface to analyze the
(Continued)

digitized electrocardiogram signals, to detect a cardiac arrhythmia based on the digitized electrocardiogram signals, and to control the therapy delivery interface to apply electrical therapy to the patient based upon the detected cardiac arrhythmia. The at least one processor is further configured to analyze a frequency domain transform of the digitized electrocardiogram signals, to determine a metric indicative of a metabolic state of a heart of the patient, and to accelerate or delay application of the electrical therapy based upon the metric.

27 Claims, 5 Drawing Sheets

(51) Int. Cl.
| | |
|---|---|
| A61N 1/362 | (2006.01) |
| A61N 1/39 | (2006.01) |
| A61N 1/04 | (2006.01) |
| A61H 31/00 | (2006.01) |
| A61B 5/361 | (2021.01) |
| A61N 1/365 | (2006.01) |
| A61B 5/0205 | (2006.01) |
| A61B 5/30 | (2021.01) |

(52) U.S. Cl.
CPC ......... *A61B 5/7257* (2013.01); *A61H 31/005* (2013.01); *A61N 1/046* (2013.01); *A61N 1/0484* (2013.01); *A61N 1/3625* (2013.01); *A61N 1/36507* (2013.01); *A61N 1/3925* (2013.01); *A61N 1/39044* (2017.08); *A61N 1/3968* (2013.01); *A61N 1/3987* (2013.01); *A61N 1/3993* (2013.01); *A61B 5/0205* (2013.01); *A61B 5/303* (2021.01); *A61B 2505/01* (2013.01); *A61B 2562/17* (2017.08); *A61B 2562/221* (2013.01); *A61H 2031/001* (2013.01); *A61H 2031/002* (2013.01); *A61H 2201/0184* (2013.01); *A61H 2201/10* (2013.01); *A61H 2201/165* (2013.01); *A61H 2201/1619* (2013.01); *A61H 2201/1652* (2013.01); *A61H 2201/1654* (2013.01); *A61H 2201/5007* (2013.01); *A61H 2201/5025* (2013.01); *A61H 2201/5043* (2013.01); *A61H 2201/5046* (2013.01); *A61H 2201/5048* (2013.01); *A61H 2201/5079* (2013.01); *A61H 2201/5097* (2013.01); *A61H 2230/00* (2013.01); *A61H 2230/045* (2013.01); *A61H 2230/06* (2013.01); *A61H 2230/08* (2013.01); *A61H 2230/207* (2013.01); *A61H 2230/30* (2013.01); *A61H 2230/42* (2013.01); *A61H 2230/60* (2013.01); *A61H 2230/65* (2013.01)

(58) Field of Classification Search
CPC .......... A61B 2562/221; A61B 5/04286; A61B 2505/01; A61B 5/361; A61B 5/303; A61N 1/0484; A61N 1/3986; A61N 1/3993; A61N 1/3925; A61N 1/36507; A61N 1/39044; A61N 1/046; A61N 1/3987; A61N 1/3625; A61N 1/3968; A61H 31/005; A61H 2230/00; A61H 2201/5079; A61H 2230/65; A61H 2230/60; A61H 2240/42; A61H 2230/30; A61H 2230/207; A61H 2230/08; A61H 2230/42; A61H 2230/06; A61H 2230/045; A61H 2201/5097; A61H 2201/5048; A61H 2201/5046; A61H 2201/5043; A61H 2201/5025; A61H 2201/5007;
A61H 2201/1654; A61H 2201/1652; A61H 2201/165; A61H 2201/1619; A61H 2201/10; A61H 2031/002; A61H 2031/001; A61H 2201/0184
See application file for complete search history.

(56) References Cited

U.S. PATENT DOCUMENTS

| | | | |
|---|---|---|---|
| 5,092,341 | A | 3/1992 | Kelen |
| 5,741,304 | A | 4/1998 | Patwardhan et al. |
| 5,944,669 | A | 8/1999 | Kaib |
| 5,957,856 | A | 9/1999 | Weil et al. |
| 6,019,877 | A * | 2/2000 | Dupelle ............... A61N 1/0492 204/196.11 |
| 6,148,233 | A | 11/2000 | Owen |
| 6,171,257 | B1 | 1/2001 | Weil et al. |
| 6,224,562 | B1 | 5/2001 | Lurie et al. |
| 6,760,621 | B2 | 7/2004 | Walcott |
| 6,813,517 | B2 | 11/2004 | Daynes et al. |
| 7,269,454 | B2 | 9/2007 | Sherman |
| 7,593,772 | B2 | 9/2009 | Sherman |
| 7,774,060 | B2 | 8/2010 | Westenkow |
| 7,813,791 | B1 | 10/2010 | Gill |
| 7,831,299 | B2 | 11/2010 | Tan et al. |
| 7,920,917 | B2 | 4/2011 | Kelly |
| 8,165,671 | B2 | 4/2012 | Freeman et al. |
| 8,868,179 | B2 | 10/2014 | Quau et al. |
| 8,948,859 | B2 | 2/2015 | Freeman et al. |
| 8,989,837 | B2 | 3/2015 | Weinstein et al. |
| 9,180,304 | B2 | 11/2015 | Quan et al. |
| 9,186,521 | B2 | 11/2015 | Quan et al. |
| 9,480,853 | B2 | 11/2016 | Quan et al. |
| 9,579,515 | B2 | 2/2017 | Quau et al. |
| 9,592,402 | B2 | 3/2017 | Quau et al. |
| 9,782,093 | B2 | 10/2017 | Quan et al. |
| 9,907,477 | B2 | 3/2018 | Quan et al. |
| 2002/0026229 | A1 | 2/2002 | Weil et al. |
| 2002/0133197 | A1 | 9/2002 | Snyder et al. |
| 2002/0138106 | A1 | 9/2002 | Chiristini et al. |
| 2003/0055460 | A1 | 3/2003 | Owen et al. |
| 2004/0039419 | A1* | 2/2004 | Stickney ............... A61B 5/046 607/5 |
| 2004/0116969 | A1 | 6/2004 | Owen |
| 2004/0215271 | A1 | 10/2004 | Sullivan |
| 2005/0080828 | A1 | 5/2005 | Johnson |
| 2005/0245974 | A1 | 11/2005 | Sherman |
| 2005/0267536 | A1 | 12/2005 | Freeman et al. |
| 2006/0025824 | A1 | 2/2006 | Freeman |
| 2006/0116724 | A1 | 6/2006 | Synder |
| 2007/0060785 | A1 | 3/2007 | Freeman et al. |
| 2007/0100381 | A1 | 5/2007 | Snyder et al. |
| 2008/0145827 | A1 | 6/2008 | Strand et al. |
| 2008/0208070 | A1 | 8/2008 | Snyder et al. |
| 2009/0270930 | A1* | 10/2009 | Walker ................ A61N 1/3904 607/5 |
| 2009/0281413 | A1 | 11/2009 | Boyden |
| 2010/0268059 | A1 | 10/2010 | Ryu et al. |
| 2010/0298899 | A1* | 11/2010 | Donnelly ........... A61N 1/37258 607/6 |
| 2011/0021938 | A1 | 1/2011 | Anderson et al. |
| 2011/0034816 | A1 | 2/2011 | Tan et al. |
| 2011/0202100 | A1 | 8/2011 | Tan et al. |
| 2011/0202101 | A1 | 8/2011 | Tan et al. |
| 2011/0295127 | A1 | 12/2011 | Sandler et al. |
| 2012/0010543 | A1 | 1/2012 | Johnson et al. |
| 2012/0046706 | A1 | 2/2012 | Anderson et al. |
| 2012/0191024 | A1 | 7/2012 | Halperin et al. |
| 2012/0226178 | A1 | 9/2012 | Freeman et al. |
| 2013/0138168 | A1 | 5/2013 | Quan et al. |
| 2013/0144181 | A1 | 6/2013 | Fogt et al. |
| 2013/0190634 | A1 | 7/2013 | Phillips |
| 2013/0218057 | A1 | 8/2013 | Jorgenson |
| 2013/0331719 | A1 | 12/2013 | Freeman |
| 2014/0005738 | A1* | 1/2014 | Jorgenson ........... A61N 1/3925 607/7 |

(56) References Cited

U.S. PATENT DOCUMENTS

| | | | |
|---|---|---|---|
| 2014/0107541 A1* | 4/2014 | Sullivan | A61B 5/7217 601/41 |
| 2014/0236030 A1 | 8/2014 | Tan et al. | |
| 2014/0277224 A1 | 9/2014 | Quan et al. | |
| 2014/0277228 A1 | 9/2014 | Quan et al. | |
| 2015/0065815 A1* | 3/2015 | Najarian | A61B 5/7203 600/301 |
| 2015/0461002 | 5/2015 | Freeman et al. | |
| 2015/0257709 A1 | 9/2015 | Quan et al. | |
| 2015/0257715 A1 | 9/2015 | Quan et al. | |
| 2015/0352367 A1 | 12/2015 | Quan et al. | |
| 2015/0352369 A1 | 12/2015 | Quan et al. | |
| 2016/0023010 A1 | 1/2016 | Quan et al. | |
| 2016/0082278 A1 | 3/2016 | Quan et al. | |
| 2017/0209706 A1 | 7/2017 | Quan et al. | |
| 2017/0348538 A1 | 12/2017 | Quan | |
| 2017/0361120 A1 | 12/2017 | Liu | |
| 2018/0000368 A1 | 1/2018 | Quan | |
| 2018/0220913 A1 | 8/2018 | Quan et al. | |
| 2018/0304088 A1 | 10/2018 | Quan et al. | |
| 2019/0054307 A1 | 2/2019 | Quan et al. | |
| 2019/0261878 A1 | 8/2019 | Quan | |
| 2019/0282823 A1 | 9/2019 | Freeman | |
| 2019/0365264 A1 | 12/2019 | Freeman | |

FOREIGN PATENT DOCUMENTS

| | | | |
|---|---|---|---|
| WO | WO 2011/100534 | 8/2011 | |
| WO | WO 2012/059846 | 5/2012 | |
| WO | WO 2012/072518 | 6/2012 | |
| WO | WO 2013/071280 | 5/2013 | |
| WO | WO-2015101878 A1 * | 7/2015 | A61B 5/7207 |

OTHER PUBLICATIONS

Chaudhry, Fahd A., A Novel Resuscitation Algorithm Using Waveform Analysis and End-Tidal Carbon Dioxide Pressure for Ventricular Fibrillation, University of Arizona, Biomedical Engineering Interdisciplinary Program, 2011, 39 pages.
Chinese Office Action, CN Application 201480027256.X, dated May 30, 2016, 8 pages.
Compos et al., "An Up-Down Bayesian, Defibrillation Efficacy Estimator", Pace—Pacing and Clinical Electrophysiology, Blackwell Futura Publishing, Malden, MA, US, vol. 20, No. 5, Part 01, May 1, 1997, pp. 1292-1300.
European Search Report, 14768658.8, dated Feb. 12, 2016, 10 pages.
Extended European Search Report, PCT/US2012/065779, dated Aug. 14, 2015, 7 pages.
Extended European Search Report, European Patent Application No. 13804051.4, dated Feb. 4, 2016, 9 pages.
Huang et al, "Quantification of activation patterns during ventricular fibrillation in open-chest porcine left ventricle and septum". Heart Rhythm Elsevier, US, vol. 2, No. 7, Jul. 1, 2005, pp. 720-728.
International Search Report and Written Opinion, PCT/US2012/64779, dated Feb. 1, 2013, 8 pages.
International Search Report and Written Opinion, PCT/US2014/027431, dated Aug. 11, 2014, 14 pages.
International Search Report and Written Opinion, PCT/US2014/27514, dated Aug. 11, 2014, 8 pages.
International Search Report and Written Opinion, PCT/US2014/27658, dated Aug. 25, 2014, 19 pages.
International Search Report and Written Opinion, PCT/US2015/35174, dated Sep. 17, 2015, 13 pages.
International Search Report and Written Opinion, PCT/US2015/35189, dated Nov. 3, 2015, 20 pages.
International Search Report and Written Opinion from corresponding PCT/US2013/44750 dated Sep. 20, 2013.
Lee, Seungyup, "Mapping the Characteristics of Atrial Activation Patterns During Atrial Fibrillation," Case Western Reserve University: Department of Biomedical Engineering, Jan. 2013, 34 pages.
Povoas et al., "Predicting the success of defibrillation by electrocardiographic analysis," Resuscitation 53(1):77-82 (2002).
Watson et al., "Rapid Communication: Wavelet transform-based prediction of the likelihood of successful defibrillation for patients exhibiting ventricular fibrillation: Rapid Communication", Measurement Science and Technology, IOP, Bristol, GB, vol. 16, No. 10, Oct. 1, 2005, pp. L1-L6.
European Patent Office, Supplementary European Search Report, dated Nov. 4, 2016 for EP Application No. 14768107.6, 8 pages.
International Preliminary Report on Patentability issued in international application No. PCT/US2016/023992, dated Sep. 26, 2017, 9 pages.
U.S. Office Action in U.S. Appl. No. 15/658,908, dated Jul. 2, 2018, 8 pages.
U.S. Office Action in U.S. Appl. No. 15/868,277, dated Jun. 4, 2018, 6 pages.
Wang et al., "Fourier Analysis in Polar and Spherical Coordinates," Internal Report Jan. 2008, Albert-Ludwigs University Freiburg, 2008, 26 pages.
Wang, et al., "Rotational Invariance Based on Fourier Analysis in Polar and Spherical Coordinates," IEEE Transactions on Pattern Analysis and Machine Intelligence, vol. 31, No. 9, Sep. 2009.

* cited by examiner

AMPLITUDE SPECTRUM AREA CONSIDERATIONS FOR AN EXTERNAL MEDICAL MONITORING AND TREATMENT DEVICE

TECHNICAL FIELD

The technology described in this document is directed to non-invasive medical devices, and more particularly, to a non-invasive ambulatory medical monitoring and treatment device that is capable of externally defibrillating and/or externally pacing the heart of a patient wearing the device.

BACKGROUND

Cardiac arrest and other cardiac health ailments are a major cause of death worldwide. Various resuscitation efforts aim to maintain the body's circulatory and respiratory systems during cardiac arrest in an attempt to save the life of the victim. Such resuscitation efforts may include CPR (i.e., chest compressions with or without artificial respiration), pacing, defibrillation, drug therapy, open heart massage, or various combinations thereof. For many forms of cardiac arrest, such as where the subject is suffering from Ventricular Fibrillation (VF) or Ventricular Tachycardia (VT), defibrillation may be appropriate, especially if applied soon after the onset of VF or VT. Various studies have shown that each minute of delay in the application of defibrillation can result in a 10% decrease in the victim's chance of survival, thus the sooner the resuscitation efforts begin, the better the victim's chances of survival.

SUMMARY

In one aspect, this document features an ambulatory medical monitoring and treatment device. The device includes a power source, a therapy delivery interface coupled to the power source, and a plurality of therapy electrodes coupled to the therapy delivery interface. The device also includes a plurality of electrocardiogram (ECG) sensing electrodes to sense ECG signal of a heart of a patient, a sensor interface to receive and digitize the ECG signal, and at least one processor coupled to the sensor interface and the therapy delivery interface. The at least one processor is configured to analyze the ECG signal, wherein the analysis includes determining a metric based on an analysis of at least one channel of the ECG signal. The metric is indicative of a general viability of the heart or indicative of chances of success of a therapeutic intervention to reduce cardiac arrhythmia. The at least one processor is further configured to detect a cardiac arrhythmia based on the analysis of the ECG signal, and control the therapy delivery interface to apply electrical therapy to the patient based upon the detected cardiac arrhythmia. Such controlling includes modifying a timing or choice of the therapeutic intervention based upon the metric. Implementations can include one or more of the following features.

The therapeutic intervention can include defibrillation, cardiopulmonary resuscitation (CPR), or pacing. The metric can be determined based on analyzing a plurality of channels of the ECG signal. The metric can be determined based on a transform-based analysis of the ECG signal. The metric can also be determined based on an area of an amplitude spectrum (AMSA). The metric can also be determined or based on time domain measurements. The metric can include median slope. The transform can be one of: a Fourier transform, a wavelet transform, or a Hilbert transform. The metric can include an area of an amplitude spectrum of ventricular fibrillation waveforms obtained from a frequency domain transform of the digitized ECG signal. The metric can be determined over a window of time of 100 milliseconds to twenty seconds. The at least one processor can be configured to accelerate the application of the electrical therapy to the patient in response to the metric indicating general viability of the heart or a threshold probability of success of the therapeutic intervention to reduce cardiac arrhythmia. The application of the electrical therapy to the patient can be delayed in response to the metric indicating an absence of general viability of the heart or a low chance of success of the therapeutic intervention to reduce cardiac arrhythmia. The device can include a user interface coupled to the at least one processor, wherein the at least one processor is further configured to issue instructions via the user interface requesting CPR be performed on the patient in response to the metric indicating the absence of general viability of the heart or the low chance of success of the therapeutic intervention to reduce cardiac arrhythmia. The application of electrical therapy to the patient can be delayed in response to a determination that CPR is being performed on the patient.

The at least one processor can be further configured to determine a first metric indicative of the general viability of the heart or the chances of success of a therapeutic intervention to reduce cardiac arrhythmia during a first time period. The at least one processor can also be configured to determine a second metric indicative of the general viability of the heart or the chances of success of a therapeutic intervention to reduce cardiac arrhythmia of the patient during a second time period that is subsequent to the first time period. The processor can also be configured to compare the first metric to the second metric, and to accelerate the application of the electrical therapy to the patient in response to the second metric being less than the first metric by a threshold amount. The metric can be determined for a first period of time. The metric can also be determined for at least one second period of time that is shorter than the first period of time to determine when the electrical therapy is to be applied to the patient. The first period of time can be approximately two seconds, and each second period of time can be approximately 200 milliseconds. The at least 200 milliseconds period of time can include successive overlapping windows. The electrical therapy can be applied to the patient at time corresponding to a local maximum of the area of the amplitude spectrum of the ventricular fibrillation waveform.

Aspects and embodiments of the present technology are directed to a medical monitoring and treatment device that monitors a cardiac condition of a patient and can administer external therapy to the heart. In certain embodiments the functionality may be performed by a non-invasive bodily-attached ambulatory medical monitoring and treatment device. In contrast to currently available monitoring and treatment devices, embodiments of the present technology use an analysis of the spectral area of electrocardiogram (ECG) waveforms of the patient to hasten or delay the application of electrical therapy based on the spectral analysis. In certain embodiments, the analysis of the spectral area of the ECG waveforms may be combined with the monitoring of other physiological parameters of the patient, such as muscle activity, to hasten or delay the application of electrical therapy, and/or to recommend an alternative treatment, such as the performance of cardiopulmonary resuscitation (CPR), be performed on the patient.

The metric can be determined over multiple intervals of time, and the device can be configured to control the therapy delivery interface to apply defibrillation to the patient at a time corresponding to a local indicia of the sequence of determined values of the metric. The intervals can be successive. The intervals can be at least partially overlapping or consecutive. The intervals can be 100 milliseconds to 1 second in duration. The indicia can be a maximum, or a minimum. The indicia can be based on a first, second or higher order derivative or difference of the sequence of determined values of the metric. Each of the plurality of successive windows of time can be approximately 1 second in duration. The plurality of successive windows of time can overlap one another by approximately two hundred milliseconds. The plurality of successive windows of time can be non-overlapping. The at least one processor can be configured to determine a local indicia of the sequence of determined values of the metric over the plurality of successive windows of time and control the therapy delivery interface to apply defibrillation to the patient when the most recent determined value of the metric differs from the local indicia by more than a predetermined amount.

In another aspect, the document features a method that includes receiving ECG signals from a heart of a patient using a non-invasive bodily-attached ambulatory medical monitoring and treatment device, and analyzing the ECG signals to detect a cardiac arrhythmia. Such analysis can include analyzing a frequency domain transform of the ECG signals to determine a metric indicative of a general viability of the heart or indicative of chances of success of a therapeutic intervention to reduce cardiac arrhythmia. The method also includes determining whether to apply electrical therapy to the heart of the patient based on the detected cardiac arrhythmia, and accelerating or delaying the electrical therapy to the heart of the patient based upon the metric.

Implementations can include one or more of the following features.

The detected cardiac arrhythmia can be ventricular fibrillation and the electrical therapy can be accelerated in response to the metric indicating a general viability of the heart or a threshold probability of success of the therapeutic intervention to reduce cardiac arrhythmia. The electrical therapy can be delayed in response to the metric indicating an absence of general viability of the heart or a low chance of success of the therapeutic intervention to reduce cardiac arrhythmia. The electrical therapy can include defibrillation. Analyzing the frequency domain transform of the ECG signals can include analyzing the frequency domain transform of the ECG signals obtained over a window of time of a particular length to determine the metric. The length of the time window can be approximately one second, approximately two seconds, approximately three seconds or approximately four seconds. The window of time can be a first window, wherein a frequency domain transform of the ECG signals obtained over a plurality of second windows of time is analyzed to determine when to apply the electrical therapy to the heart of the patient. Each second window of time of the plurality of second windows of time can be approximately one second in duration. The plurality of second windows of time can be adjacent and overlap one another by approximate 200 milliseconds. Analyzing the frequency domain transform of the ECG signals over the plurality of second windows of time can include determining an area of an amplitude spectrum of ventricular fibrillation waveforms obtained from the frequency domain transform of the ECG signals over each second window of time. The electrical therapy can be applied to the heart of the patient at a time corresponding to local maxima of the area of the amplitude spectrum of the ventricular fibrillation waveforms obtained from the frequency domain transform of the ECG signals over each second window of time. Analyzing the frequency domain transform of the ECG signals can include analyzing the frequency domain transform of the ECG signals obtained over a window of time of approximately two seconds to determine the metric. The metric can include an area of an amplitude spectrum of ventricular waveforms obtained from the frequency domain transform of the ECG signals obtained of the window of time.

DETAILED DESCRIPTION

Figure 1:
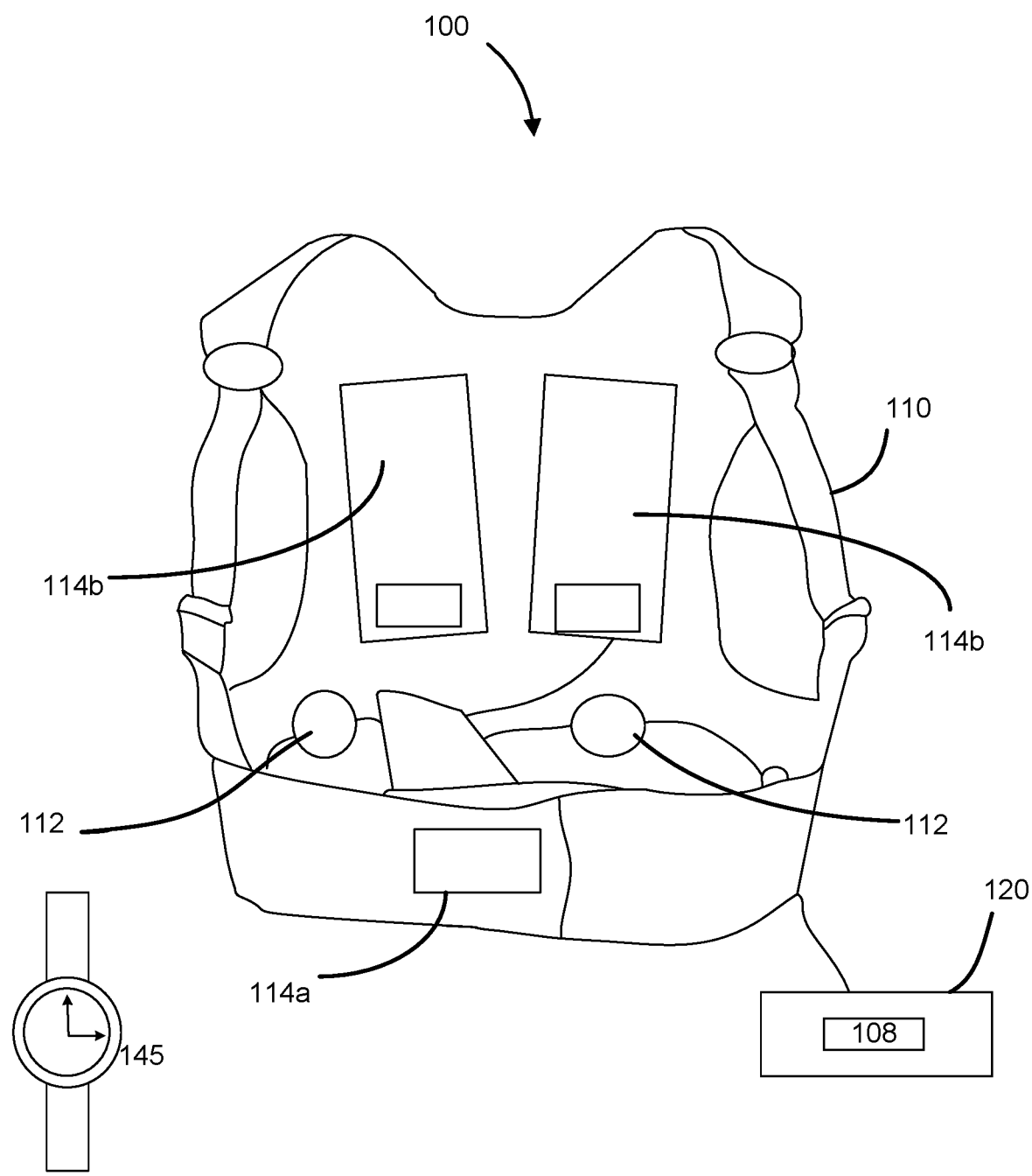
FIG. 1 illustrates a medical monitoring and treatment device, such as a wearable defibrillator.

The examples of the methods and apparatus discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Any references to examples or elements or acts of the systems and methods herein referred to in the singular may also embrace examples including a plurality of the elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Aspects and embodiments of the present technology monitor the cardiac condition of a patient and administer external therapy to the heart using a non-invasive medical monitoring and treatment device, and in some embodiments monitor the cardiac condition of a patient and administer external therapy to the heart using a bodily-attached non-invasive ambulatory medical monitoring and treatment device. In some embodiments, the technology described herein may also be used in invasive devices. As used herein, the term non-invasive means that the device does not penetrate the body of a patient. In contrast, invasive devices, such as implantable medical devices, at least a portion of the device is disposed subcutaneously. The term bodily-attached means that at least a portion of the device (other than its electrodes in the case of a defibrillator, cardioverter or pacer) is removably attached to the body of a patient, such as by mechanical coupling (for example, by a wrist strap, cervical collar, bicep ring), adhesion (for example, by an adhesive gel intermediary), suction, magnetism, fabric or other flexible material (for example, by straps or integration into a garment) or other body mounting features not limited by the aforementioned examples. The coupling elements hold the device in a substantially fixed position with respect to the body of the patient. The term ambulatory means that the device is capable of, and designed for, moving with the patient as the patient goes about their daily routine.

Although embodiments of the present technology are primarily directed to non-invasive bodily-attached ambulatory medical monitoring and treatment devices, various aspects of the present technology may be adapted for use in other types of non-invasive medical monitoring and treatment devices that are not adapted to be worn by a patient, such as an Automated External Defibrillator (AED) or an Advanced Life Support (ALS) type of defibrillator, such as the M Series defibrillator, R Series ALS defibrillator, R Series Plus defibrillator, or E Series defibrillator manufactured by the ZOLL Medical Corporation of Chelmsford Mass.

One example of a non-invasive bodily-attached ambulatory medical monitoring and treatment device (hereinafter referred to as a "medical monitoring and treatment device") is the LifeVest® Wearable Cardioverter Defibrillator available from ZOLL Medical Corporation of Chelmsford, Mass. The medical monitoring and treatment device can provide lifesaving defibrillation treatment to a patient suffering from a treatable form of cardiac arrhythmia such as Ventricular Fibrillation (VF) or Ventricular Tachycardia (VT).

FIG. 1 illustrates a medical monitoring and treatment device, such as a LifeVest® Wearable Cardioverter Defibrillator available from ZOLL Medical Corporation of Chelmsford, Mass. As shown, the medical monitoring and treatment device 100 includes a harness 110 having a pair of shoulder straps and a belt that is worn about the torso of a patient. The harness 110 is typically made from a material, such as cotton, nylon, spandex, or combinations thereof that is breathable, and unlikely to cause skin irritation, even when worn for prolonged periods of time. The medical monitoring and treatment device 100 includes a plurality of electrocardiographic (ECG) sensing electrodes 112 that are disposed on or in the harness 110 at various positions about the patient's body and electrically coupled (wirelessly or by a wired connection) to a portable treatment controller 120 via a connection pod. The plurality of ECG sensing electrodes 112 are used by the portable treatment controller 120 to monitor the cardiac function of the patient and generally include a front/back pair of ECG sensing electrodes and a side/side pair of ECG sensing electrodes. In some embodiments, additional ECG sensing electrodes may be provided, and the plurality of ECG sensing electrodes 112 may be disposed at varying locations about the patient's body. In addition, the plurality of ECG electrodes 112 may incorporate any electrode system, including conventional stick-on adhesive electrodes, dry-sensing capacitive ECG electrodes, radio transparent electrodes, segmented electrodes, or one or more long term wear electrodes that are configured to be continuously worn by a patient for extended periods (e.g., 3 or more days). Signals from various combinations of pairs of the plurality of ECG electrodes can be used to define different channels of the ECG signal. For example, signals measured using a particular pair of electrodes can be used to obtain a differential signal to define a corresponding channel of the ECG signal. The medical monitoring and treatment devices disclosed herein may incorporate sundry materials arranged in a variety of configurations to maintain a proper fit with the patient's body. Thus embodiments are not limited to the configuration and materials described above with reference to FIG. 1.

The medical monitoring and treatment device 100 can include a plurality of therapy electrodes 114 that are electrically coupled to the portable treatment controller 120 via the connection pod and which are configured to deliver one or more therapeutic defibrillating shocks to the body of the patient, if it is determined that such treatment is warranted. In some embodiments, the plurality of therapy electrodes may also be configured to perform cardiac pacing, or to apply an electrical shock that can terminate a cardiac arrhythmia, such as VT. As shown, the plurality of therapy electrodes 114 includes a first therapy electrode 114a that is disposed on the front of the patient's torso and a second therapy electrode 114b that is disposed on the back of the patient's torso. The second therapy electrode 114b may, as shown, include a pair of therapy electrodes that are electrically coupled together and act as the second therapy electrode 114b. The use of two therapy electrodes 114a, 114b permits a biphasic shock to be delivered to the body of the patient, such that a first of the two therapy electrodes can deliver a first phase of the biphasic shock with the other therapy electrode acting as a return, and the other therapy electrode can deliver the second phase of the biphasic shock with the first therapy electrode acting as the return. The connection pod electrically couples the plurality of ECG sensing electrodes 112 and the plurality of therapy electrodes 114 to the portable treatment controller 120, and may include electronic circuitry. For example, in one implementation the connection pod includes signal acquisition circuitry, such as a plurality of differential amplifiers to receive ECG signals from different ones of the plurality of ECG sensing electrodes 112 and to provide a differential ECG signal to the portable treatment controller 120 based on the difference therebetween. The connection pod may also include other electronic circuitry, such as a motion sensor or accelerometer by which patient activity may be monitored. A motion sensor may also be disposed in the portable treatment controller 120 to change the orientation of the display upon a change in the orientation of the portable treatment controller, to detect a drop or abuse event, etc.

In some embodiments, both the first therapy electrode 114a and the second therapy electrode 114b are disposed on the front of the patient's torso. For example, the first therapy electrode 114a may be located at external to the apex of the heart and the second therapy electrode 114b may be located along the parasternal line. Thus embodiments are not limited to a particular arrangement of therapy electrodes 114.

In some embodiments, the plurality of ECG sensing electrodes 112 are positioned and paired such that artifacts generated from electrical activity are decreased. In other embodiments, the electronic circuitry included in the portable treatment controller 120 may equalize artifacts measured at electrodes by changing a gain or impedance.

As shown in FIG. 1, the medical monitoring and treatment device 100 may also include a user interface pod that is electrically coupled to the portable treatment controller 120. The user interface pod can be attached to the patient's clothing or to the harness 110, for example, via a clip (not shown) that is attached to a portion of the interface pod. Alternatively, the user interface pod may simply be held in a person's hand, or may be integrated into a watch 145 that communicates wirelessly with the portable treatment controller 120. In some embodiments, the user interface pod may communicate wirelessly with the user interface 108 of the ambulatory medical device controller 120, for example, using a Bluetooth®, Wireless USB, ZigBee, Wireless Ethernet, GSM, or other type of communication interface. The user interface pod typically includes one or more actionable user interface elements (e.g., one or more buttons, a fingerprint scanner, a touch screen, microphone, etc. . . . ) by which the patient, or a bystander can communicate with the portable treatment controller 120, and a speaker by which the portable treatment controller 120 may communicate with the patient or the bystander. In certain models of the LifeVest® Wearable Cardioverter Defibrillator, the functionality of the user interface pod is incorporated into the portable treatment controller 120, and the portable treatment controller 120 includes an LCD display.

The portable treatment controller 120 generally includes at least one processor, microprocessor, or controller, such as a processor commercially available from companies such as Texas Instruments, Intel, AMD, Sun, IBM, Motorola, Freescale and ARM Holdings. In one implementation, the at least one processor includes a power conserving processor arrangement that includes a general purpose processor, such as an Intel® PXA270 processor and a special purpose processor, such as a Freescale™ DSP56311 Digital Signal Processor. The at least one processor of the portable treatment controller 120 is configured to monitor the patient's medical condition, to perform medical data logging and storage, and to provide medical treatment to the patient in response to a detected medical condition, such as cardiac arrhythmia.

Although not shown, the medical monitoring and treatment device 100 may include additional sensors, other than the ECG sensing electrodes 112, capable of monitoring the physiological condition or activity of the patient. For example, sensors capable of measuring blood pressure, heart rate, heart sounds, thoracic impedance, pulse oxygen level, respiration rate, muscle activity (e.g., electromyographic or EMG sensors), and the activity level or body position of the patient may also be provided.

In various models of the LifeVest® Wearable Cardioverter defibrillator, the portable treatment controller 120 determines whether a treatable life-threatening cardiac arrhythmia is present based primarily on an analysis of the ECG signals obtained from the patient. Such an analysis may include, for example, QRS signal detection based upon digitized ECG signals, the morphology of the detected QRS signals and the patient's heart rate, axis analysis of patient's heart using vector cardiographic techniques, and the spectral analysis of various frequency components of patient's ECG signals, such as described in U.S. Pat. No. 5,944,669 (the "'669 patent"), which is hereby incorporated by reference herein. An arrhythmia detection component that is executable on the portable treatment controller 120 evaluates the various ECG metrics, as well as other metrics to determine a confidence level of whether a treatable arrhythmia exists. Other metrics that are evaluated by the arrhythmia detection component typically include the signal to noise ratio of the ECG signals, the correlation between detected anomalies in the ECG signal and the presence of noise, a correlation between detected anomalies in the ECG signal and motion of the patient, as well as the general activity level of the patient. If the confidence level of the detected arrhythmia exceeds a determined threshold, the portable treatment controller activates a treatment component configured to provide treatment to the patient.

Activation of the treatment component generally includes a charging of capacitors that are operatively coupled to the treatment electrodes and capable of storing sufficient energy to provide one or more defibrillating shocks to the body of the patient. The capacitors are typically disposed within the portable treatment controller and coupled to a power source, such as a battery, that is also typically disposed within the controller. In some embodiments, the capacitors, and/or the battery may be separate from the portable treatment controller; for example, the capacitors may be located on opposing sides of the patient's torso for better weight distribution and comfort. In response to detection of the treatable cardiac arrhythmia and the charging of the capacitors, the portable treatment controller generally issues an audible alarm or alert via a loudspeaker (not shown) on the portable treatment controller 120 and/or the user interface pod alerting the patient and any bystanders to the patient's medical condition. The alert is generally repeated one or more times during and after the charging of the capacitors and the continued detection of the arrhythmia. In the event that the detected arrhythmia continues, and even after the capacitors are fully charged to an energy level capable of providing one or more defibrillating shocks to the body of the patient, the portable treatment controller 120 instructs the patient to press and hold one or more buttons on the portable treatment controller 120 or on the user interface pod or watch 145 to indicate that they are conscious, thereby instructing the portable treatment controller 120 to withhold the delivery of one or more therapeutic defibrillating shocks. If the patient does not respond, the device presumes that the patient is unconscious or otherwise incapacitated and in need of treatment, and proceeds with the treatment sequence, culminating in the delivery of one or more defibrillating shocks to the body of the patient.

Although various models of the LifeVest® Wearable Cardioverter Defibrillator can provide a defibrillating shock within 45 seconds from the detection of the onset of a detected cardiac arrhythmia such as VF, in some situations it can be advantageous to hasten, or to delay, the administration of electrical therapy to a patient. Accordingly, a review of ECG data obtained from a number of patients was conducted to determine whether other forms of ECG analysis, and other physiological parameters of the patient could be used to determine whether to hasten or delay the administration of treatment.

In one set of experiments conducted by Applicants, ECG data from a number of patients was analyzed using a variety of different ECG analysis techniques. Of the data samples evaluated, the ECG data from approximately fifteen patients was analyzed in detail. The vast majority of those patients initially exhibited VT, which then degraded to VF. A spectral analysis of the VF waveforms obtained from the electrocardiograms (ECGs) of the patients showed that in a majority of the patients, the area of the amplitude spectrum (ASA or AMSA, and simply referred to as AMSA hereafter) of the VF waveform declined by about one third from a value of approximately 35 mV*Hz at the detected onset of VF to a value of approximately 25 mV*Hz approximately 45 seconds after the detected onset of VF. In general, subjects with an AMSA value of about 21 mV*Hz or more have a statistically good chance of survival with typical interventions, such as defibrillation, while those with an AMSA value of approximately 12 mV*Hz have about a 50% chance of survival, and those with AMSA values below about 7 mV*Hz are statistically unlikely to survive.

In accordance with the experiments and analysis, a non-invasive wearable medical monitoring and treatment device is provided that analyzes ECG signals received from a patient using QRS signal detection, morphology of detected QRS signals and the patient's heart rate, axis analysis, and spectral analysis of various frequency components of the patient's ECG signal as described in the '669 patent, but which in addition monitors an area of the amplitude spectrum (AMSA) of the VF waveform obtained from the digitized ECG signals, to determine whether the application of electrical therapy, such as defibrillation, can be hastened or delayed, and whether to recommend another type of intervention, such as CPR. In addition to AMSA, one or more other metrics that are indicative of the general viability of the heart, or indicative of the chances of success of a therapeutic intervention to terminate the lethal arrhythmia can be used. Examples of such metrics include quantitative waveform measures (QMM), median slope (MS), and logarithm of the absolute correlations (LAC). Other frequency-based or transform-based metrics, such as metrics based on wavelet transforms or Hilbert transforms, can also be used in determining types and/or amount of intervention.

An advantage to the use of the AMSA of the VF waveform as a metric to hasten or delay the administration of electrical therapy, such as defibrillation, is that AMSA values may be determined from an ECG that is obtained during the performance of chest compressions, and further, the subject's ECG may be filtered (e.g., using a band pass filter with a pass band between approximately 2 to 40 Hz) to remove artifacts relating to chest compressions without impacting the predictive capability of the AMSA values calculated therefrom. In accordance with embodiments of the present technology, the medical monitoring and treatment device may also monitor the patient's ECG signals to detect the onset of VT, and provide therapy to the patient, in the form of a low-level electrical shock to induce conversion to sinus rhythm, or in the form of pacing, to reduce the possibility of VF.

Figure 2:
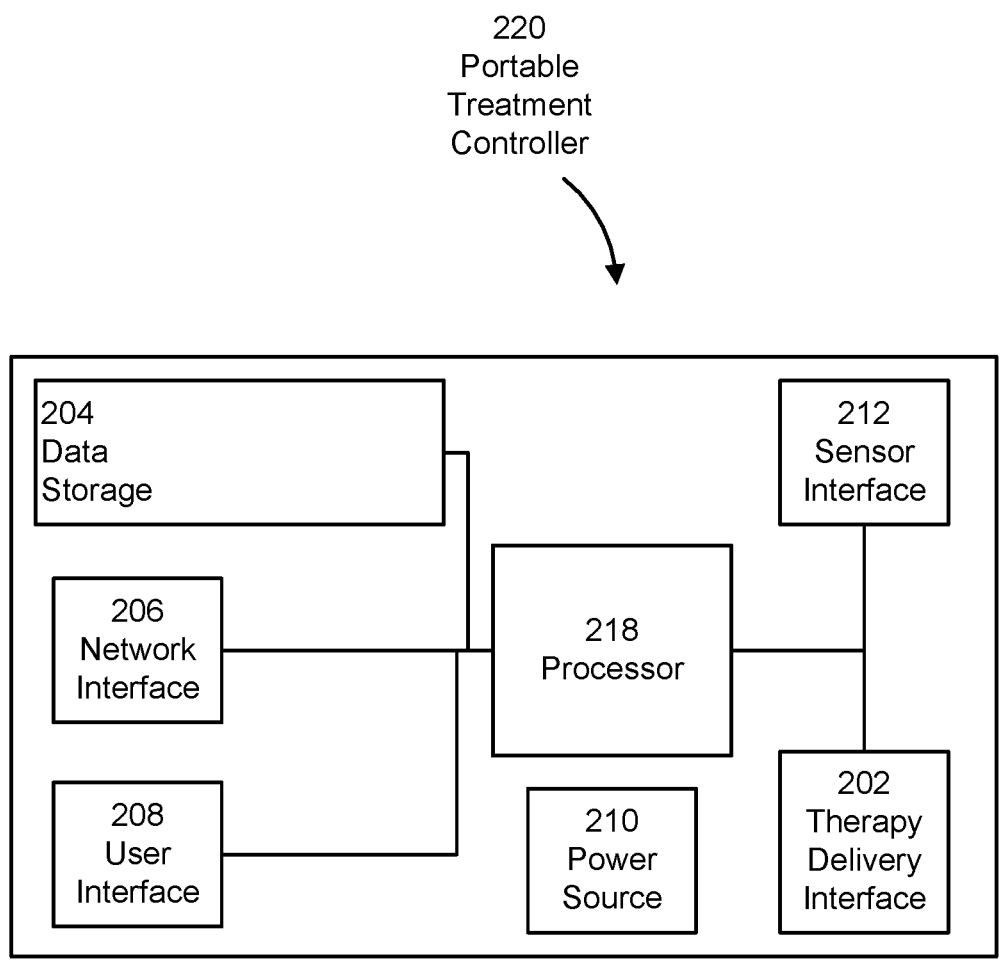
FIG. 2 is a functional block diagram of one example of a portable treatment controller that may be used in the medical monitoring and treatment device of FIG. 1.

FIG. 2 illustrates a portable treatment controller 220 that is configured to perform the critical functions of monitoring physiological information, such as ECG signals for abnormalities and initiating treatment of detected abnormalities in accordance with an aspect of the present technology. As shown, the portable treatment controller 220 includes at least one processor 218, such as a processor commercially available from companies such as Texas Instruments, Intel, AMD, Sun, IBM, Motorola, Freescale, and ARM Holdings. In one implementation, the at least one processor 218 includes a power conserving processor arrangement that includes a general purpose processor, such as an Intel® PXA270 processor and a special purpose processor, such as a Freescale™ DSP56311 Digital Signal Processor. Such a power conserving processor arrangement is described in co-pending application Ser. No. 12/833,096, titled SYSTEM AND METHOD FOR CONSERVING POWER IN A MEDICAL DEVICE, filed Jul. 9, 2010 which is incorporated by reference herein in its entirety. The at least one processor 218 of the portable treatment controller 220 is configured to monitor patient's ECG signals, to perform medical data logging and storage, to detect various cardiac arrhythmias, and to provide lifesaving defibrillation treatment to a patient suffering a treatable form of cardiac arrhythmia, such as Ventricular Fibrillation (VF) or Ventricular Tachycardia (VT).

The portable treatment controller 220 further includes a sensor interface 212, a therapy delivery interface 202, data storage 204, a communication network interface 206, a user interface 208, and a power source 210, such as a battery. In the illustrated example, the power source 210 is a rechargeable 3 cell 2200 mAh lithium ion battery pack that provides electrical power to the other device components with a minimum 24 hour runtime between charges. Such a battery has sufficient capacity to administer one or more therapeutic shocks and the therapy delivery interface 202 has wiring suitable to carry the load to the therapy electrodes 114. Moreover, in the example shown, the battery has sufficient capacity to deliver up to 5 or more therapeutic shocks, even at battery runtime expiration. The amount of power capable of being delivered to a patient during a defibrillating shock is substantial, for example up to approximately 200 Joules.

The sensor interface 212, the therapy delivery interface 202, the data storage 204, the network interface 206, and the user interface 208 are coupled to the at least one processor 218 by, for example, a bus. In the example shown, the data storage 204 includes a computer readable and writeable nonvolatile data storage medium configured to store non-transitory instructions and other data. The medium may, for example, be optical disk, magnetic disk or flash memory, among others and may be permanently affixed to, or removable from, the portable treatment controller 220.

The user interface 208 shown in FIG. 2 includes a combination of hardware and software components that allow the portable treatment controller 220 to communicate with an external entity, such as a user. The components are configured to receive information from actions such as physical movement, verbal intonation or thought processes. In addition, the components of the user interface 208 can provide information to external entities. Examples of the components that may be employed within the user interface 208 include keyboards, mouse devices, trackballs, microphones, electrodes, touch screens, printing devices, display screens speakers, computer-enabled glasses, watches, or earpieces.

As shown in FIG. 2, the portable treatment controller 220 includes several system interface components 202, 206 and 212. Each of the system interface components is configured to exchange, i.e., send or receive data, with specialized devices that may be located within the portable treatment controller 220 or elsewhere. The components used by the interfaces 202, 206 and 212 may include hardware components, software components or a combination of both. In the instance of each interface, the components physically and logically couple the portable treatment controller 220 to one or more specialized devices. The physical and logical coupling enables the portable treatment controller 220 to both communicate with and, in some instances, control the operation of specialized devices. The specialized devices may include physiological sensors, therapy delivery devices, and computer networking devices.

According to various examples, the hardware and software components of the interfaces 202, 206 and 212 employ a variety of coupling and communication techniques. In some examples, the interfaces 202, 206 and 212 use leads, cables or other wired connectors as conduits to exchange data between the portable treatment controller 220 and specialized devices. In other examples, the interfaces 202, 206 and 212 communicate with specialized devices using wireless technologies such as radio frequency or infrared technology. The software components included in the interfaces 202, 206 and 212 enable the at least one processor to communicate with specialized devices. The software components may include elements such as objects, executable code and populated data structures. Together, the hardware and software components provide interfaces through which the at least one processor 218 can exchange information with the specialized devices. Moreover, in at least some examples where one or more specialized devices communicate using analog signals, the interfaces 202, 206 and 212 can include components configured to convert analog information into digital information, and vice-versa.

As discussed above, the system interface components 202, 206 and 212 shown in the example of FIG. 2 support different types of specialized devices. For instance, the components of the sensor interface 212 couple the at least one processor 218 to one or more physiological sensors such as a body temperatures sensors, activity sensors (e.g., accelerometers), pulse oxygen sensors, thoracic impedance sensors, blood pressure sensors, acoustic sensors, respiration monitors, muscle activity (electromyographic or EMG) sensors 216 (other than ECG sensors), and dry-capacitive ECG sensing electrodes 112. In some embodiments, other types of ECG sensing electrodes may be used, such as gelled or non-gelled adhesive-backed ECG sensing electrodes, as the present technology is not limited to any particular type of ECG sensing electrode. Signal processing circuitry within the sensor interface 212 buffers, amplifies, and in some embodiments, filters the subject's ECG signal, and samples of the processed ECG signal are digitized by an A/D converter and provided to the at least one processor 218. The sensor interface 212 can typically include one or more amplifiers to buffer, amplify, and/or filter the ECG signals of the subject and an Analog to Digital (A/D) converter to sample and digitize the patient's ECG signal and provide the digitized samples of the ECG signal to the at least one processor, although one or more of the functions could alternatively be performed elsewhere in the portable treatment controller 220.

The at least one processor 218 analyzes the digitized ECG signals to determine whether a normal cardiac rhythm is present, and if not, to determine whether a cardiac condition that is treatable by defibrillation (such as VT or VF) is present. Information from the digitized ECG signals that is analyzed can include the morphology of detected QRS signals and the patient's heart rate, axis analysis, and spectral analysis of various frequency components of the patient's ECG signal as described in the '669 patent. The at least one processor 218 may display the digitized ECG signal on a display associated with the user interface 208. In response to the at least one processor 218 determining that a treatable cardiac condition is present, the processor 218 transforms the time domain samples of the subject's ECG signal to the frequency domain, for example, by using a fast Fourier transform (FFT), and calculates one or more metrics that are based upon an spectral analysis of the transformed ECG signal. In accordance with an aspect of the present technology, the metrics that are calculated by the at least one processor 218 include AMSA values which are indicative of the probability of successful defibrillation and the metabolic state of the patient's myocardium, although other metrics, such as the area of the power spectrum (PSA) could alternatively be used.

The components of the therapy delivery interface 202 couple one or more therapy delivery devices, such as capacitors and defibrillator electrodes, to the at least one processor 218. In addition, the components of the network interface 206 couple the at least one processor 218 to a computer network via a networking device, such as a bridge, router or hub. The network interface 206 may supports a variety of standards and protocols, examples of which include USB, TCP/IP, Ethernet, Wireless Ethernet, Bluetooth, ZigBee, M-Bus, IP, IPV6, UDP, DTN, HTTP, FTP, SNMP, CDMA, NMEA and GSM. To ensure data transfer is secure, in some examples, the treatment controller 220 can transmit data via the network interface 206 using a variety of security measures including, for example, TSL, SSL or VPN. In other examples, the network interface 206 includes both a physical interface configured for wireless communication and a physical interface configured for wired communication.

Figure 3:
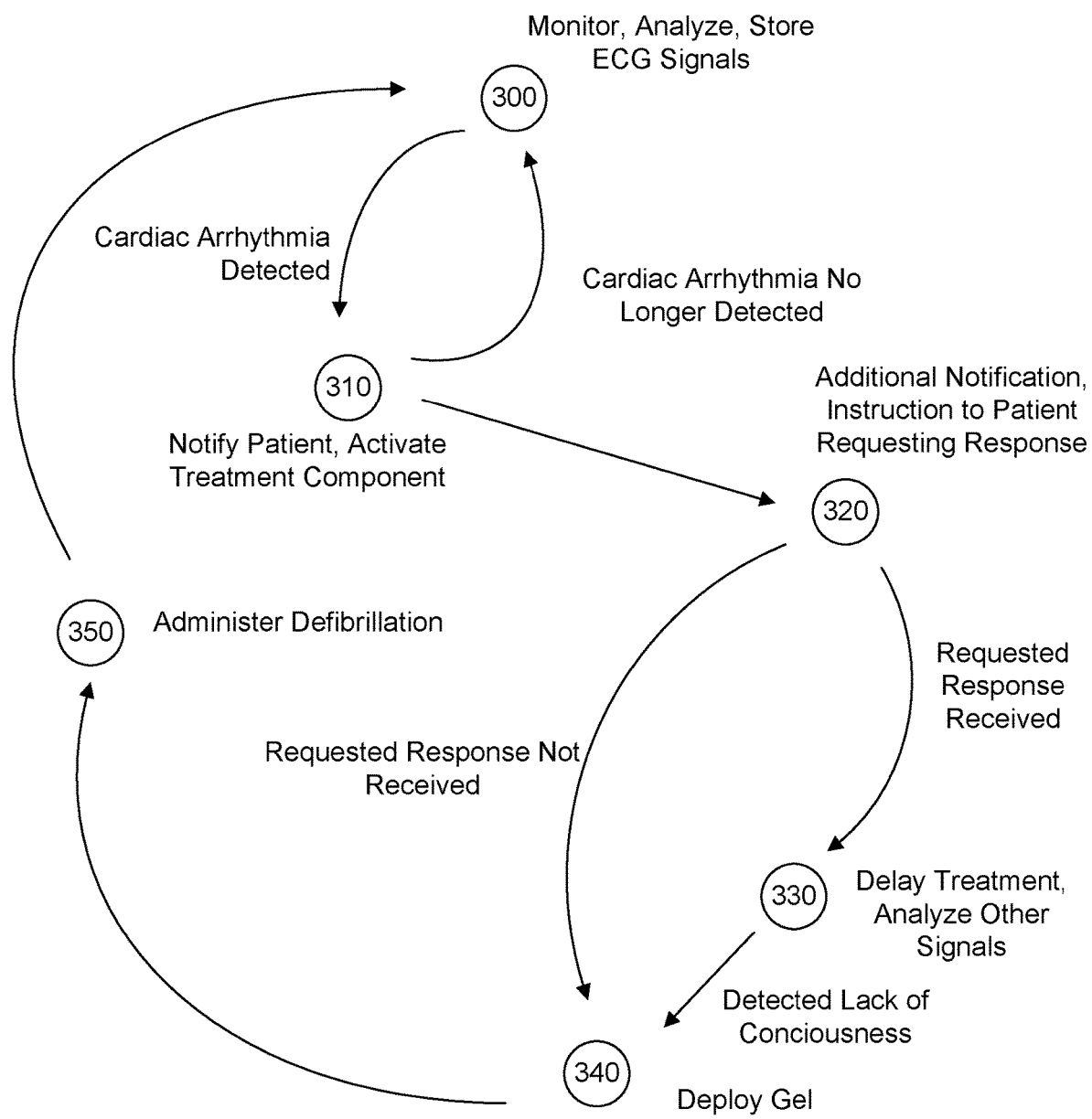
FIG. 3 is a state diagram showing various states of operation of a non-invasive, bodily attached ambulatory medical monitoring and treatment device.

FIG. 3 is a state diagram showing the various states of operation of a non-invasive bodily-attached ambulatory medical monitoring and treatment device, such as by currently available models of the LifeVest® Wearable Cardioverter Defibrillator. In state 300, which is the normal operating state of the device, the portable treatment controller monitors, analyzes, and records ECG signals obtained from the body of the patient. The analysis that is performed in state 300 generally includes QRS signal detection based upon digitized ECG signals, analyzing the morphology of the detected QRS signals and the patient's heart rate, axis analysis of patient's heart using vector cardiographic techniques, and the spectral analysis of various frequency components of patient's ECG signals, such as described in the '669 patent. In response to detecting a cardiac arrhythmia in state 300, the operation of the medical monitoring and treatment device proceeds to state 310.

In state 310, the portable treatment controller notifies the patient, and any bystanders that may be in the immediate vicinity of the patient, that it has detected a cardiac arrhythmia. The notification can include an audible alarm such as a siren, a verbal notification such as a reproduced voice command (for example, identifying that a cardiac arrhythmia has been detected), a printed message displayed on a visual display screen of the portable treatment controller, the associated watch or computer-enabled glasses, a tactile notification such as vibrations produced by a motor with an unbalanced weight on its shaft, or all of the above. In state 310, the portable treatment controller also activates a treatment component in preparation for providing one or more defibrillating shocks to the body of the patient. Activation of the treatment component generally includes the charging of one or more capacitors from a power supply of the medical monitoring and treatment device up to a level sufficient to provide one or more defibrillating shocks to the body of the patient via the therapy delivery interface 202 and the therapy electrodes 114. In state 310, the portable treatment controller typically issues another notification to the patient and any proximate bystanders, and continues to monitor the ECG signals obtained from the patient. The notification is similar to the notification provided in state 310. After activation of the treatment component, and the issuance of one or more alerts, the portable treatment controller proceeds to state 320. In response to determining in state 310 that the cardiac arrhythmia is no longer present, the portable treatment controller returns to state 300.

In state 320 the portable treatment controller continues to monitor the ECG signals obtained from the patient. In state 320, the one or more capacitors are fully charged and capable of delivering one or more defibrillating shocks to the body of the patient. In state 320, the portable treatment controller issues another notification to the patient and any proximate bystanders. The notification may be similar to the notification provided in state 310, but is followed by instructions to the patient and any bystanders that may be present. The instructions can include, for example, audible instructions that are communicated to the patient and any bystanders via a speaker on the portable treatment controller 120, the user interface pod, or the associated watch 145. The instructions can also include textual messages displayed on a visual display screen of the portable treatment controller, the associated watch, or computer-enabled glasses. The instructions can be configured, for example, to request the patient to provide a particular response, such as to press and hold one or more response buttons on the user interface pod, the portable treatment controller 120, or the associated watch 145, to indicate whether they are conscious. The instructions can also be configured to alert any bystanders not to provide the response and to move away from the patient because defibrillation is imminent. In response to providing the requested response, the portable treatment controller continues to monitor the ECG signals obtained from the patient and proceeds to state 330. In the event that the requested response is not provided, the portable treatment controller proceeds to state 340.

In state 330 the portable treatment controller sets a timer that delays the administration of defibrillation to the patient for a predetermined time, based on the receipt of the requested response. In some embodiments, the predetermined time is approximately 10 seconds. In state 330 the portable monitoring and treatment controller continues to monitor the ECG signals obtained from the patient and in some implementations monitors and analyzes other signals indicative of whether it was the patient, or another that provided the requested response. Such other signals may include signals obtained from one or more accelerometers on the wearable monitoring and treatment device indicative of the motion (e.g. consciousness) of the patient or the inactivity (e.g., lack of consciousness) of the patient, signals received from the body of the patient during actuation of the one or more response buttons (and which uniquely identify the patient as having provided the requested response), etc. In response to determining that the other signals were provided by someone other than the patient, or the other signals, such as patient activity signals obtained from one or more of the accelerometers indicate that the patient is not conscious, the portable treatment controller proceeds to state 340.

In state 340 the portable treatment controller continues to monitor the ECG signals obtained from the body of the patient, activates an impedance reducing gel dispensing mechanism that is operatively coupled to the therapy electrodes, and proceeds to state 350. In state 350 the portable treatment controller administers a defibrillating shock to the body of the patient. After administration of the defibrillating shock in state 350, the portable treatment controller returns to state 300.

Figure 4:
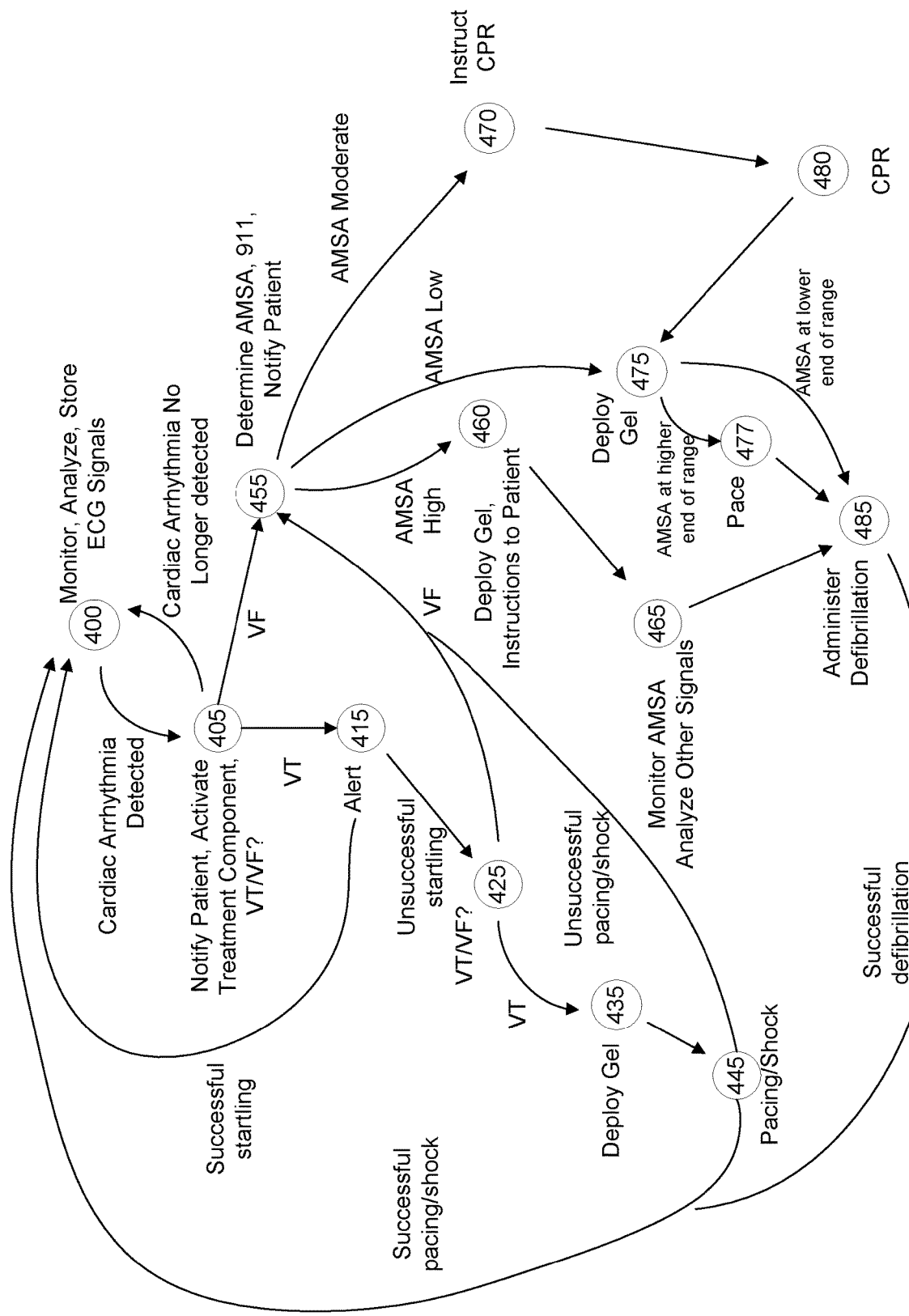
FIG. 4 is a state diagram showing various states of operation of a non-invasive, bodily attached ambulatory medical monitoring and treatment device.

FIG. 4 is a state diagram showing the various states of operation of a non-invasive ambulatory monitoring and treatment device in accordance with an embodiment of the present technology. In contrast to the operation described with respect to FIG. 3, various states of operation of the monitoring and treatment device of the embodiment also consider additional information, such as AMSA values of the VF waveform to determine whether to hasten or delay the application of a defibrillating shock to the patient. In state 400, which is the normal operating state of the device, the portable treatment controller monitors, analyzes, and records ECG signals obtained from the body of the patient. The analysis that is performed in state 400 generally includes QRS signal detection based upon digitized ECG signals, analyzing the morphology of the detected QRS signals and the patient's heart rate, axis analysis of patient's heart using vector cardiographic techniques, and the spectral analysis of various frequency components of patient's ECG signals, such as described in the '669 patent, and as described above with respect to FIG. 3. In response to detecting a cardiac arrhythmia in state 400, the operation of the medical monitoring and treatment device proceeds to state 405.

In state 405, the portable treatment controller notifies the patient, and any bystanders that may be in the immediate vicinity of the patient, that it has detected a cardiac arrhythmia. The notification can include the notifications previously described with respect to state 310, such as an audible alarm, a verbal notification, a textual message (e.g., displayed on a visual display screen of the portable treatment controller, the associated watch, or computer-enabled glasses), a tactile notification, or a combination of the above. In state 405, the portable treatment controller also activates a treatment component in preparation for providing one or more defibrillating shocks to the body of the patient. As previously described, activation of the treatment component generally includes the charging of one or more capacitors from a power supply of the medical monitoring and treatment device up to a level sufficient to provide one or more defibrillating shocks to the body of the patient via the therapy delivery interface 202 and the therapy electrodes 114. In state 405, the portable treatment controller continues to monitor the ECG signals obtained from the patient, but also makes a determination as to whether the detected cardiac arrhythmia corresponds to a treatable type of VT, or to VF. In response to determining that the detected cardiac arrhythmia corresponds to a treatable type of VT, the portable treatment controller proceeds to state 415, and in response to determining that the detected type of cardiac arrhythmia corresponds to VF, the portable treatment controller proceeds to state 455. In response to determining in state 405 that the cardiac arrhythmia is no longer present, the portable treatment controller returns to state 400.

In state 415 the one or more capacitors are fully charged and capable of delivering one or more defibrillating shocks to the body of the patient, and the portable treatment controller continues to monitor the ECG signals obtained from the patient. In state 415, in response to determining that the detected cardiac arrhythmia corresponds to a treatable type of VT, the portable treatment controller issues another notification (i.e., a high intensity alert) to the patient and any proximate bystanders. The notification may be similar to the notification provided in state 405, but is provided at a significantly increased intensity (e.g., volume level and/or vibration level), in an attempt to terminate VT and return the patient's heart to a sinus rhythm. In response to determining that VT treatment was successful, the portable treatment controller returns to state 400. Alternatively, in response to determining that VT treatment did not return the patient to a viable perfusing cardiac rhythm, the portable treatment controller proceeds to state 425.

In state 425, the portable treatment controller continues to monitor the ECG signals obtained from the patient and again makes a determination as to whether the detected cardiac arrhythmia corresponds to a treatable type of VT, or to VF. In response to determining that the detected cardiac arrhythmia corresponds to a treatable type of VT, the portable treatment controller proceeds to state 435. Alternatively, in response to determining that the detected cardiac arrhythmia has degraded from VT to VF the portable treatment controller proceeds to state 455.

In state 435, in response to determining that the detected cardiac arrhythmia corresponds to a treatable form of VT, the portable treatment controller continues to monitor the ECG signals obtained from the body of the patient. The portable treatment controller also activates an impedance reducing gel dispensing mechanism that is operatively coupled to the therapy electrodes in preparation for the administration of a low-level electrical shock configured to terminate VT, or the administration of external pacing configured to prevent the onset of VF. After activation of the impedance reducing gel, the portable treatment controller proceeds to state 445.

In state 445, the portable treatment controller continues to monitor the ECG signals obtained from the patient and based on that monitoring, makes a determination as to whether to administer a relatively low-level shock (e.g., 1 mA to 20 mA) to the body of the patient in an attempt to treat VT and to return the patient to a perfusing rhythm, to apply pacing to the body of the patient in an attempt to gain control of the patient's heart, or both. The pacing that may be applied to the heart of the patient in state 445 may include pacing the heart of a patient at a fixed rate and fixed energy, or pacing the heart of the patient using an adjustable rate and/or energy level (e.g., capture management pacing), such as overdrive pacing. In overdrive pacing, a series of pacing pulses (e.g., between about 5 and 10 pacing pulses) are delivered to the patient at a frequency above the detected intrinsic heart rate of the patient in an effort to gain control of the patient's heart rate, and which once in control of the patient's heart rate, the rate (i.e., the frequency) of the pulses are decremented until the detected intrinsic cardiac rate of the patient is at or below a typical heart rate of the patient. In response to determining that the low-level shock and/or pacing administered in state 445 is effective at returning the patient's heart to a perfusing rhythm, the portable treatment controller returns to state 400. Alternatively, in response to determining that the low-level shock and or pacing is not successful, and the patient degrades to VF, the portable treatment controller proceeds to state 455.

In response to determining in any of states 405, 425, or 445 that the detected cardiac arrhythmia corresponds to VF, the portable treatment controller proceeds to state 455. In state 455, the one or more capacitors are fully charged and capable of delivering one or more defibrillating shocks to the body of the patient and the portable treatment controller continues to monitor the ECG signals obtained from the body of the patient. The portable treatment controller sends a communication (e.g., cellular or wireless) via the communication network interface 206 (FIG. 2) to alert an emergency responder as to the status and location of the patient. In state 455, the portable treatment controller additionally determines AMSA values indicative of the metabolic state of patient's heart. As described previously, the determination of AMSA values may be based on time domain samples of the patient's ECG signals that are transformed to the frequency domain, for example, using an FFT transform, by a processor of the portable treatment controller, such as a DSP processor. In accordance with an aspect of the present technology, the AMSA values may be determined over a time window of approximately one to six seconds. Dependent upon the AMSA values determined by the portable treatment controller in state 455, and how the AMSA values change over time, the operation of the portable treatment controller may vary. For example, in response to determining that the patient's AMSA values are relatively high (about 21 mV*Hz or more) and reflect high metabolic state of the heart of the patient and a high probability of successful defibrillation, the portable treatment controller proceeds to state 460. In response to determining that the patient's AMSA values are low (below about 10 mV*Hz or more) and reflect a low metabolic state of the heart of the patient and a low probability of successful defibrillation, the portable treatment controller proceeds to state 475. In response to determining that the patient's AMSA values are intermediate (between approximately 10 mV*Hz and 20 mV*Hz), the portable treatment controller proceeds to state 470.

In state 460, the portable treatment controller continues to monitor the ECG signals obtained from the body of the patient and determines updated AMSA values indicative of the metabolic state of patient's heart. The portable treatment controller activates the impedance reducing gel dispensing mechanism that is operatively coupled to the therapy electrodes in preparation for the administration of a defibrillating shock (if it has not been previously activated in state 435), and issues instructions to the patient and any bystanders that may be present. The instructions can include, for example, audible instructions that are communicated to the patient and any bystanders via a speaker on the portable treatment controller 120, the user interface pod, and/or the associated watch 145. The instructions can also include textual messages displayed on a visual display screen of the portable treatment controller, the associated watch, or computer-enabled glasses. The instructions can be configured, for example, to request the patient to provide a particular response, such as to press and hold one or more response buttons on the user interface pod, the portable treatment controller 120, or the associated watch 145, to indicate whether they are conscious. The instructions can also be configured to alert any bystanders not to provide the response and to move away from the patient because defibrillation is imminent. The portable treatment controller sets a timer (e.g., 10 seconds) to await a response from the patient, and proceeds to state 465.

In state 465, the portable treatment controller continues to monitor the ECG signals obtained from the patient and determines updated AMSA values. In response to determining that the updated AMSA values have not changed (i.e., declined) appreciably from those determined in states 455 and 460, the portable treatment controller may await the requested response from the patient, analyze other signals that may be indicative of the consciousness or lack of consciousness of the patient and expiration of the timer before proceeding to state 485. Alternatively, if the AMSA values determined in state 465 have decreased appreciably (e.g., by about 10% or more) from those determined in state 460, the requested response has not been received by the patient, and other signals (such as information from one or more accelerometers) are indicative of a lack of consciousness, or signals from other sensors such as EMG sensors indicate the presence of a seizure (often a precursor to a lack of consciousness), the portable treatment controller proceeds immediately to state 485 and does not await expiration of the timer.

In state 485, the portable treatment controller administers a defibrillating shock to the body of the patient. After administration of the defibrillating shock in state 485, the portable treatment controller may return to state 400 if it is determined that the defibrillation was successful. However, dependent on AMSA values, the portable treatment controller may instead deliver another defibrillating shock. For example, if AMSA values were at a relatively high level prior to defibrillation, and the defibrillation shock does not appear to have been effective, the portable treatment controller may deliver another defibrillating shock within as little as 10 seconds or less after the initial defibrillating shock. The is because although it may take as much as 40-45 second to determine whether a defibrillating shock was successful, it takes significantly less time to determine whether a defibrillating shock was not successful.

In response to determining in state 455 that the patient's AMSA values are low (below about 10 mV*Hz or more), the portable treatment controller proceeds to state 475, wherein the portable treatment controller activates the impedance reducing gel dispensing mechanism (if it has not been previously activated in state 435) that is operatively coupled to the therapy electrodes in preparation for the administration of a defibrillating shock. Because the determined low AMSA values reflect a relatively low probability of survival and a defibrillation shock may be the patient's best chance at survival, the portable treatment controller then proceeds immediately to state 485 in an attempt to save the life of the patient, wherein the portable treatment controller administers a defibrillating shock to the body of the patient. In the event that the defibrillating shock is not successful, the portable treatment controller proceeds to state 470.

In some embodiments, the portable treatment controller need not proceed immediately to state 485 after deploying the impedance reducing gel in state 475. For example, in response to determining that the patient's AMSA values are low, but near the higher end of the scale (e.g., between 8-10 mV*Hz or so), the portable treatment controller may optionally proceed to state 477. In state 477, the portable treatment controller may continue to monitor the ECG signals obtained from the patient and apply pacing to the body of the patient in an attempt to gain control of the patient's heart. The pacing that may be applied to the heart of the patient in state 477 may include pacing the heart of a patient at a fixed rate and fixed energy, or pacing the heart of the patient using an adjustable rate and/or energy level (e.g., capture management pacing), such as described previously. In response to determining that the pacing was not successful, the portable treatment controller proceeds to state 485.

Alternatively, in response to determining in state 455 that the patient's AMSA values are intermediate (between approximately 10 mV*Hz and 20 mV*Hz), but not indicative of a high probability of success, the portable treatment controller proceeds to state 470. In state 470, the portable treatment controller continues to monitor the ECG signals obtained from the body of the patient and determines updated AMSA values indicative of the metabolic state of patient's heart. The portable treatment controller also issues instructions, such as by a textual message on a visual display screen of the portable treatment controller or the associated watch, and audible instructions to any proximate bystanders, to perform CPR on the patient in an effort to improve the metabolic state of the patient's heart so that defibrillation is more likely to be effective. After issuing the instructions to perform CPR on the patient, the portable treatment controller proceeds to state 480.

In state 480, the portable treatment controller continues to monitor the ECG signals obtained from the body of the patient and determines updated AMSA values indicative of the metabolic state of patient's heart. The portable treatment controller also monitors signals, such as those provided by the one or more accelerometers provided on the wearable treatment device, to determine whether CPR is being administered to the patient. In the event that the portable treatment controller determines that CPR is being administered to the patient, the portable treatment controller may continue to monitor the ECG signals and continue to determine AMSA values to detect whether the administration of CPR is having a beneficial effect. In the event that the CPR is having a beneficial effect, the portable treatment controller may continue to monitor the ECG signals and determine updated AMSA values until the probability of successful defibrillation (as indicated by the updated AMSA values) increases to a point where defibrillation is likely to be successful. In response to determining that defibrillation has a sufficiently high probability of success, the portable treatment controller may instruct the bystander to discontinue CPR and move away from the patient, so that the impedance reducing gel may be deployed in state 475 and a defibrillation shock administered in state 485. Alternatively, in response to determining by the portable treatment controller that CPR is not being administered to the patient, the portable treatment controller may proceed immediately to states 475 and 485.

Although the ability to use additional metrics of the metabolic state of a patient's heart, such as AMSA values, to vary the type of therapy, and the timing of that therapy is particularly well suited to a non-invasive, ambulatory medical monitoring and treatment device, such as the LifeVest® cardioverter defibrillator, such functionality could also be implemented in an Automated External Defibrillator (AED) or an Advanced Life Support (ALS) type of defibrillator, such as the M Series defibrillator, R Series ALS defibrillator, R Series Plus defibrillator, or E Series defibrillator manufactured by the ZOLL Medical Corporation of Chelmsford Mass.

In the above described embodiments, AMSA values are determined over a window of time of approximately one to six seconds. The determined AMSA values are generally indicative of the metabolic state of the patient's heart, with higher AMSA values reflecting a better metabolic state. However, in other embodiments, AMSA values may be determined over a shorter period of time, such as a window of time of two seconds, or even one second. Such windows of time may be successive windows of time that do not overlap with one another, or they may be overlapping windows of time in which one window overlaps in time with a successive window by, for example, approximately 200 milliseconds. Even if AMSA values determined over such shorter windows of time are not adequately indicative of the metabolic state of a patient's heart, they can be used in predicting whether an intervention, such as defibrillation, might be successful at restoring a perfusing cardiac rhythm. In particular, AMSA values determined over a shorter window of time can be used to determine when to apply the intervention to the body of the patient to increase the probability of restoring a perfusing cardiac rhythm.

In a second set of experiments, ECG data from the above experiments was again analyzed using a variety of different ECG analysis techniques. A spectral analysis of the VF waveforms obtained from the ECGs of the approximately fifteen patients that initially exhibited VT and which then degraded into VF was again performed, and AMSA values were determined. However, the AMSA values determined in the second set of experiments were determined over progressively shorter windows of time. In the second set of experiments, as the window of time over which the AMSA values were determined became progressively shorter, the variation in AMSA value from one window to the next became more pronounced. Based on the second set of experiments, Applicants identified that during early stages of VF, AMSA values determined over a window of time of approximately one second changed significantly from one window to the next. When the AMSA values obtained over successive windows of time were analyzed over a period of time of about six seconds or more, the variation in AMSA values exhibited a generally sinusoidal shape, increasing and then decreasing in value in a periodic manner. In analyzing the AMSA values of those patients in which defibrillation was successful relative to those in which defibrillation was not successful, Applicants determined that defibrillation was successful at restoring a perfusing cardiac rhythm when the defibrillation was applied at a time corresponding to locally maximum AMSA values, as opposed to other times, and in particular, as opposed to times corresponding to locally minimum AMSA values.

In accordance with a further aspect of the present technology, AMSA values determined over various length windows of time may be used to determine whether the application of electrical therapy, such as defibrillation, can be expedited or delayed. In response to determining that electrical therapy can be applied, it is determined when such electrical therapy can be applied to the patient to increase the probability of a successful intervention. For example, AMSA values determined over a window of approximately one to four seconds may be used to determine whether to expedite or delay the application of electrical therapy. AMSA values determined over a smaller window of approximately one second may be used to identify when to apply that electrical therapy to increase the probability of successful intervention.

Figure 5:
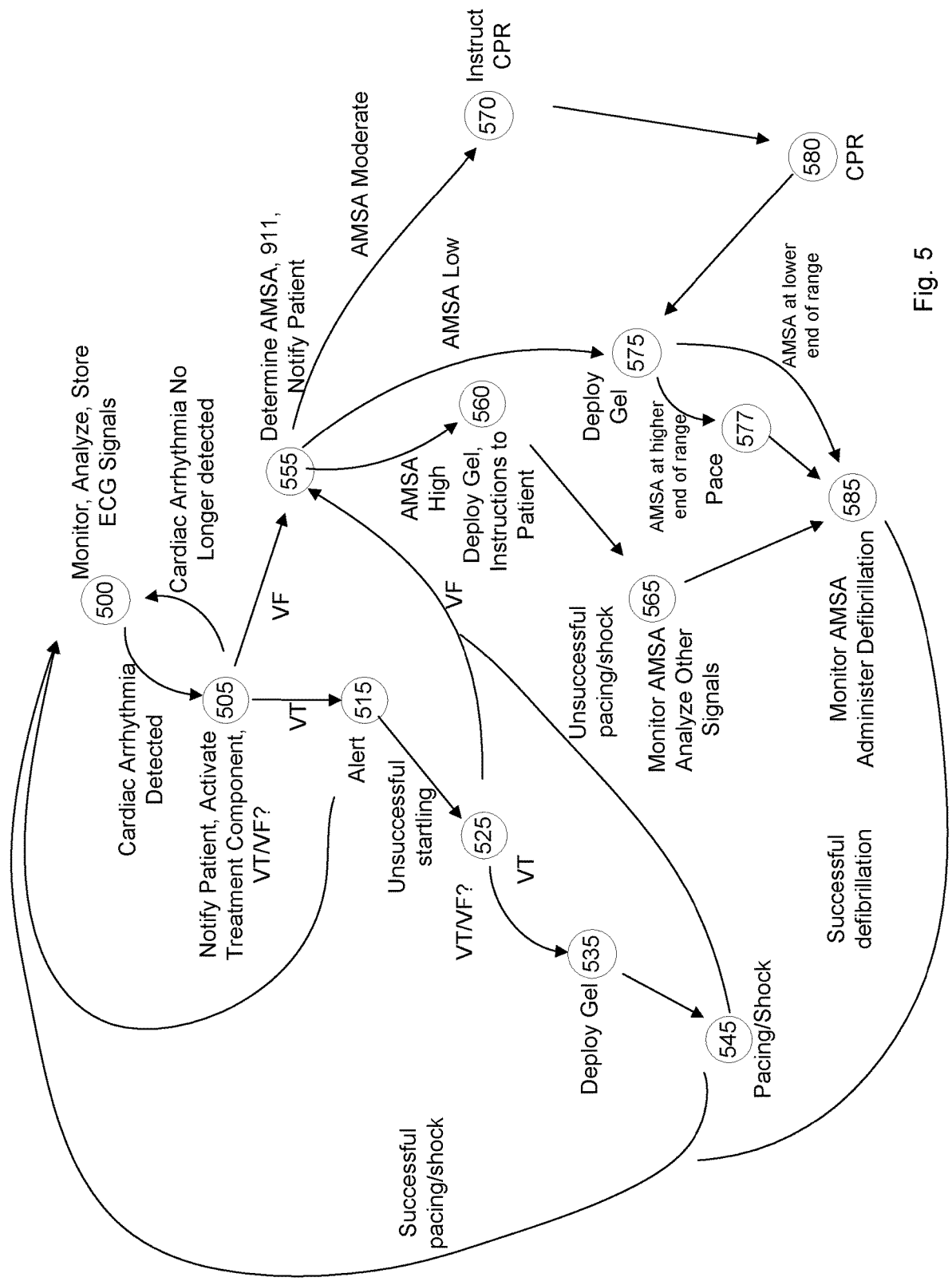
FIG. 5 is a state diagram showing various states of operation of a non-invasive, bodily attached ambulatory medical monitoring and treatment device.

FIG. 5 is a state diagram showing the various states of operation of a non-invasive ambulatory monitoring and treatment device in accordance with another embodiment of the present technology. The various states shown in FIG. 5 generally correspond to similar states described above with respect to FIG. 4, and are designated by similar reference numerals (e.g., state 505 in FIG. 5 corresponds to state 405 in FIG. 4, state 555 in FIG. 5 corresponds to state 455 in FIG. 4, etc.) Accordingly, those states of operation that are similar to those described previously with respect to FIG. 4 are described only briefly herein.

As in the embodiment described with respect to FIG. 4, the various states of operation of the monitoring and treatment device of the embodiment also consider additional information, such as AMSA values of the VF waveform to determine whether to hasten or delay the application of a defibrillating shock to the patient. As in the embodiment described with respect to FIG. 4, such AMSA values are determined over a relatively long window of time, such as two seconds, and are generally indicative of the metabolic state of the patient's myocardium. However, various states of operation of the embodiment further determine AMSA values over shorter windows of time, and use those AMSA values to identify when electrical therapy can be applied.

In state 500, which is the normal operating state of the device, the portable treatment controller monitors, analyzes, and records ECG signals obtained from the body of the patient. As noted previously, the analysis generally includes QRS signal detection based upon digitized ECG signals, analyzing the morphology of the detected QRS signals and the patient's heart rate, axis analysis of patient's heart, and the spectral analysis of various frequency components of patient's ECG signals. In response to determining that a cardiac arrhythmia is detected in state 500, the medical monitoring and treatment device proceeds to state 505 wherein the portable treatment controller notifies the patient, and any bystanders, that it has detected a cardiac arrhythmia. The notification can be audible, verbal, written (e.g., a textual message displayed on a visual display screen of the portable treatment controller, the associated watch or computer-enabled glasses), tactile, or all of the above.

In state 505, the portable treatment controller also activates a treatment component in preparation for providing one or more defibrillating shocks to the body of the patient. As previously described, the generally includes charging of one or more capacitors to a level sufficient to provide one or more defibrillating shocks to the body of the patient via the therapy delivery interface 202 and the therapy electrodes 114. In state 505, the portable treatment controller continues to monitor the ECG signals obtained from the patient, and also makes a determination as to whether the detected cardiac arrhythmia corresponds to a treatable type of VT, or to VF. In response to determining that the detected cardiac arrhythmia corresponds to a treatable type of VT, the portable treatment controller proceeds to state 515. In response to determining that the detected type of cardiac arrhythmia corresponds to VF, the portable treatment controller proceeds to state 555. In response to determining in state 505 that the cardiac arrhythmia is no longer present, the portable treatment controller returns to state 500.

In state 515 the portable treatment controller continues to monitor the ECG signals obtained from the patient, and in response to determining that the detected cardiac arrhythmia corresponds to a treatable type of VT, the portable treatment controller issues another notification to the patient and any proximate bystanders. As noted previously, the notification can be provided at a significantly increased intensity (e.g., volume level and/or vibration level), in an attempt to terminate VT. In response to determining that the notification is successful in returning the patient to perfusing cardiac rhythm, the portable treatment controller returns to state 500. Alternatively, in response to determining that the notification does not return the patient to a viable perfusing cardiac rhythm, the portable treatment controller proceeds to state 525.

In state 525, the portable treatment controller continues to monitor the ECG signals obtained from the patient and again makes a determination as to whether the detected cardiac arrhythmia corresponds to a treatable type of VT, or to VF. In response to determining that the detected cardiac arrhythmia still corresponds to a treatable type of VT, the portable treatment controller proceeds to state 535. Alternatively, in response to determining that the detected cardiac arrhythmia has degraded from VT to VF the portable treatment controller proceeds to state 555.

In state 535, in response to determining that the detected cardiac arrhythmia corresponds to a treatable form of VT, the portable treatment controller continues to monitor the ECG signals obtained from the body of the patient and activates the impedance reducing gel dispensing mechanism that is operatively coupled to the therapy electrodes in preparation for the administration of a low-level shock configured to terminate VT, or the administration of external pacing. The portable treatment controller then proceeds to state 545.

In state 545, the portable treatment controller continues to monitor the ECG signals obtained from the patient and based on that monitoring, makes a determination as to whether to administer a relatively low-level shock (e.g., 1 mA to 20 mA) to the body of the patient in an attempt to terminate VT and to return the patient to a perfusing rhythm, to apply pacing to the body of the patient in an attempt to gain control of the patient's heart, or both. As described previously, the pacing applied in state 445 may include pacing the heart of a patient at a fixed rate and fixed energy, or pacing the heart of the patient using an adjustable rate and/or energy level (e.g., capture management pacing), such as overdrive pacing. In response to determining that the low-level shock and/or pacing was effective at returning the patient's heart to a perfusing rhythm, the portable treatment controller returns to state 500. Alternatively, in response to determining that the low-level shock and or pacing was not successful, and the patient degrades to VF, the portable treatment controller proceeds to state 555.

In response to determining in any of states 505, 525, or 545 that the detected cardiac arrhythmia corresponds to VF, the portable treatment controller proceeds to state 555. In state 555, the portable treatment controller continues to monitor the ECG signals obtained from the body of the patient and sends a communication (e.g., cellular or wireless) via the communication network interface 206 (FIG. 2) to alert an emergency responder as to the status and location of the patient. The portable treatment controller additionally determines AMSA values indicative of the metabolic state of patient's heart. As described previously, the determination of AMSA values may be based on time domain samples of the patient's ECG signals obtained over a time window of approximately two seconds that are transformed to the frequency domain, for example, using an FFT transform, by a processor of the portable treatment controller, such as a DSP processor. Dependent upon the AMSA values determined by the portable treatment controller in state 555, and how the AMSA values change over time, the operation of the portable treatment controller may vary. For example, in response to determining that the patient's AMSA values are relatively high (about 21 mV*Hz or more), the portable treatment controller proceeds to state 560. Alternatively, in response to determining that the patient's AMSA values are low (below about 10 mV*Hz or more), the portable treatment controller proceeds to state 575. In response to determining that the patient's AMSA values are intermediate (between approximately 10 mV*Hz and 20 mV*Hz), the portable treatment controller proceeds to state 570.

In state 560, the portable treatment controller continues to monitor the ECG signals obtained from the body of the patient and determines updated AMSA values indicative of the metabolic state of patient's heart. The portable treatment controller activates the impedance reducing gel dispensing mechanism (if it has not been previously activated in state 535), and issues instructions to the patient and any bystanders that may be present. As previously described, the instructions can include, for example, audible instructions that are communicated to the patient and any bystanders via a speaker on the portable treatment controller 120, the user interface pod, or the associated watch 145. The instructions can also include textual messages displayed on a visual display of the portable treatment controller, the associated watch, or computer-enabled glasses. The instructions can be configured to request the patient to provide a particular response, such as to press and hold one or more response buttons on the user interface pod, or on the portable treatment controller 120 or the associated watch 145, to indicate whether they are conscious. The instructions can also be configured to alert any bystanders not to provide the response and to move away from the patient because defibrillation is imminent. The portable treatment controller sets a timer (e.g., 10 seconds) to await a response from the patient, and proceeds to state 565.

In state 565, the portable treatment controller continues to monitor the ECG signals obtained from the patient and determines updated AMSA values. In response to determining that the updated AMSA values have not changed (i.e., declined) appreciably from those determined in states 555 and 560, the portable treatment controller may await the requested response from the patient, analyze other signals that may be indicative of the consciousness or lack of consciousness of the patient and expiration of the timer before proceeding to state 585. Alternatively, if the AMSA values determined in state 565 have decreased appreciably (e.g., by about 10% or more) from those determined in state 560, the requested response has not been received by the patient, and other signals (such as information from one or more accelerometers) are indicative of a lack of consciousness, or signals from other sensors such as EMG sensors indicate the presence of a seizure (often a precursor to a lack of consciousness), the portable treatment controller proceeds immediately to state 585 and does not await expiration of the timer.

In state 585, the portable treatment controller continues to monitor the ECG signals obtained from the patient and determines AMSA values. However, in state 585, the AMSA values are determined over much smaller windows of time than those determined in states 555 and 565. In accordance with an aspect of the present technology, the AMSA values determined in state 585 are based on a window of time of approximately one second in duration, and AMSA values are successively determined for a period of time of approximately six to eight seconds. The windows of time over which the AMSA values are determined in state 585 may be successive windows of time that do not overlap with one another, or they may be overlapping windows of time in which one window overlaps in time with a successive window by, for example, approximately 200 milliseconds. In state 585, the portable treatment controller monitors the AMSA values determined over successive windows (of approximately one second in duration) to determine when a defibrillation shock can be administered to the patient and then applies defibrillation to the patient at that time.

As noted previously, during early stages of VF, AMSA values determined over a window of time of approximately one second change from one window to the next in a periodic manner having a generally sinusoidal shape when viewed over a period of time of about six seconds or more. Accordingly, in state 585 the portable treatment controller monitors the AMSA values over successive windows to predict the point in time when the AMSA value is at a locally maximum value, and to apply defibrillation to the patient at that point in time when the AMSA value is a local maximum. The may be done in a number of different ways. For example, in one embodiment, the portable treatment controller determines a local minimum AMSA value over a period of about six to eight seconds, and then applies defibrillation when the AMSA values are trending upward, and have a value that satisfies a threshold condition (e.g., is 50% greater than the local minima). In another embodiment, the portable treatment controller can determine a local maximum AMSA value over the period of about six to eight seconds, and then apply defibrillation when the AMSA values are trending upward, and have a value that satisfies a threshold condition (e.g., is 75% of the local maxima). In yet another embodiment, the portable treatment controller can determine local maxima and minima AMSA values over the period of about six to eight seconds, and then apply defibrillation when the AMSA values are trending upward, and have a value that satisfies a threshold based on the determined AMSA values (e.g., is greater than the average of the local minima and the local maxima, is greater than a certain percentage of the local minima, the local maxima, or a combination of the local minima and the local maxima). In some implementations, a combination of the different approaches described above may be used to determine when the AMSA values are trending upward and approaching a local maximum, and to control the timing of the defibrillation to generally coincide with the local maximum to increase the probability of successful defibrillation. Embodiments of the present technology are not limited to any one specific approach.

In state 585, after determining when defibrillation can be applied to the body of the patient, the portable treatment controller applies defibrillation to the patient at the predicted time to increase the probability of successful defibrillation. After administration of the defibrillating shock in state 585, the portable treatment controller may return to state 500 if it is determined that the defibrillation was successful. However, dependent on AMSA values, the portable treatment controller may instead deliver another defibrillating shock as described previously with respect to FIG. 4.

In response to determining in state 555 that the patient's AMSA values are low (below about 10 mV*Hz or more), the portable treatment controller proceeds to state 575, wherein the portable treatment controller activates the impedance reducing gel dispensing mechanism (if it has not been previously activated in state 535) in preparation for the administration of a defibrillating shock. The portable treatment controller then proceeds either directly to state 585, or to state 577. For example, in response to determining that the AMSA values are low, but near the higher end of the scale (e.g., between 8-10 mV*Hz or so), the portable treatment controller may proceed to state 577, wherein pacing may be applied in the manner previously described. In response to determining that the pacing performed in state 577 was not effective, the portable treatment controller may then proceed to state 585. Alternatively, in response to determining in state 555 that the AMSA values of the patient are near the lower end of the scale (e.g., 7 mV*Hz or less), the portable treatment controller proceeds directly to state 585, as the application of defibrillation may be the patient's best chance for survival. As noted previously, in state 585, the portable treatment controller monitors AMSA values determined over smaller windows of time to predict when to apply defibrillation, and then applies the defibrillation at a time when the patient's AMSA values are trending toward a local maximum value.

In response to determining in state 555 that the patient's AMSA values are intermediate (between approximately 10 mV*Hz and 20 mV*Hz), but not indicative of a high probability of success, the portable treatment controller proceeds to state 570. In state 570, the portable treatment controller continues to monitor the ECG signals obtained from the body of the patient and determines updated AMSA values indicative of the metabolic state of patient's heart. The portable treatment controller also issues instructions, such as by a textual message on a visual display screen of the portable treatment controller or an associated watch, and audible instructions to any proximate bystanders, to perform CPR on the patient in an effort to improve the metabolic state of the patient's heart where defibrillation is more likely to be effective. After issuing the instructions to perform CPR on the patient, the portable treatment controller proceeds to state 580.

In state 580, the portable treatment controller continues to monitor the ECG signals obtained from the body of the patient and determines updated AMSA values indicative of the metabolic state of patient's heart. The portable treatment controller also monitors signals, such as those provided by the one or more accelerometers provided on the wearable treatment device, to determine whether CPR is being administered to the patient. In the event that the portable treatment controller determines that CPR is being administered to the patient, the portable treatment controller may continue to monitor the ECG signals and continue to determine AMSA values to detect whether the administration of CPR is having a beneficial effect. In the event that the CPR is having a beneficial effect, the portable treatment controller may continue to monitor the ECG signals and determine updated AMSA values until the probability of successful defibrillation (as indicated by the updated AMSA values) increases to a point where defibrillation is likely to be successful. In response to determining that defibrillation has a sufficiently high probability of success, the portable treatment controller may instruct the bystander to discontinue CPR and move away from the patient, so that the impedance reducing gel may be deployed in state 575 and a defibrillation shock administered as described previously with respect to state 585. Alternatively, in response to determining by the portable treatment controller that CPR is not being administered to the patient, the portable treatment controller may proceed immediately to states 575 and 585.

In some implementations, other metrics associated with the metabolic state of a patient's heart can also be used in various defibrillators, including defibrillators that are not non-invasive, ambulatory, and bodily attached, such as an Automated External Defibrillator (AED) or an Advanced Life Support (ALS) type of defibrillator. AMSA values obtained over varying windows of time can be used to vary the type of therapy, and the timing of that therapy in such defibrillators. For example, AMSA values determined over successive smaller windows of time of about one second can be used in making a determination about timing and type of therapy in various commercially available defibrillators, including, for example, the M Series defibrillators, R Series ALS defibrillators, R Series Plus defibrillators, or E Series defibrillators manufactured by ZOLL Medical Corporation of Chelmsford Mass. In such defibrillators, defibrillation can be applied to the patient, for example, at a time when AMSA values are trending toward a local maximum to increase the probability of successful defibrillation.

Having thus described several aspects of at least one embodiment of the technology, it is to be appreciated various alterations, modifications, and improvements can readily occur to those skilled in the art. Such alterations, modifications, and improvements are intended to be part of the disclosure, and are intended to be within the scope of the following claims.

What is claimed is:

1. An ambulatory medical monitoring and treatment device comprising:
   a harness configured to be worn about a torso of a patient's body;
   a power source;
   a therapy delivery interface, coupled to the power source;
   a plurality of therapy electrodes coupled to the therapy delivery interface;
   a plurality of electrocardiogram (ECG) sensing electrodes to sense an ECG signal of a heart of a patient, wherein the plurality of therapy electrodes and the plurality of ECG sensing electrodes are configured to be disposed on the harness such that they are at a plurality of predetermined positions about the torso of the patient's body;
   a sensor interface to receive and digitize the ECG signal; and
   at least one processor coupled to the sensor interface and the therapy delivery interface, the at least one processor configured to:
   analyze the ECG signal to generate ECG data in a time domain, transform the ECG data in the time domain to a frequency domain representation of the ECG data, determine a metric based on an analysis of the frequency domain representation of the ECG data, the metric being indicative of a general viability of the heart, and the metric comprising a value of an amplitude spectrum area (AMSA), detect a treatable cardiac arrhythmia based on the analysis of the ECG signal, instruct the patient to provide a response to the ambulatory medical monitoring and treatment device in response to detection of the treatable cardiac arrhythmia, generate a selection of a therapeutic intervention corresponding to the treatable cardiac arrhythmia, the therapeutic intervention including a selection of an electrical therapy, a delayed electrical therapy, a defibrillation, a cardiopulmonary resuscitation (CPR), a pacing, or any combination thereof, the therapeutic intervention being configured to be administered to the patient within a predetermined timing from an onset of detection of the treatable cardiac arrhythmia if the patient fails to respond to the instruction to provide a response, determine, based on the metric from the analysis of the frequency domain representation of the ECG data, whether to modify the predetermined timing, determine, based on the metric from the analysis of the frequency domain representation of the ECG data, whether to modify the selection of the therapeutic intervention, and in accordance with the determination whether to modify the predetermined timing and the determination whether to modify the selection of the therapeutic intervention, control the therapy delivery interface to apply the therapeutic intervention to the patient based upon the treatable cardiac arrhythmia.

2. The ambulatory medical monitoring and treatment device of claim 1, wherein the metric is determined based on at least one of analyzing a plurality of channels of the ECG signal or time domain measurements.

3. The ambulatory medical monitoring and treatment device of claim 1, wherein the metric is median slope.

4. The ambulatory medical monitoring and treatment device of claim 1, wherein the transform is one of: a Fourier transform, a wavelet transform, or a Hilbert transform.

5. The ambulatory medical monitoring and treatment device of claim 1, wherein the metric comprises an area of an amplitude spectrum of ventricular fibrillation waveforms obtained from a frequency domain transform of the digitized ECG signal.

6. The ambulatory medical monitoring and treatment device of claim 1, wherein the metric is determined over a window of time of 100 milliseconds to twenty seconds.

7. The ambulatory medical monitoring and treatment device of claim 6, wherein the at least one processor is configured to accelerate an application of the electrical therapy to the patient in response to the metric indicative of the general viability of the heart or a threshold probability of success of the therapeutic intervention to reduce the treatable cardiac arrhythmia.

8. The ambulatory medical monitoring and treatment device of claim 6, wherein the at least one processor is configured to delay an application of the electrical therapy to the patient in response to the metric indicating an absence of general viability of the heart or a low chance of success of the therapeutic intervention to reduce the treatable cardiac arrhythmia.

9. The ambulatory medical monitoring and treatment device of claim 6, further comprising a user interface coupled to the at least one processor, wherein the at least one processor is further configured to issue instructions via the user interface requesting CPR be performed on the patient in response to the metric indicating an absence of general viability of the heart or a low chance of success of the therapeutic intervention to reduce the treatable cardiac arrhythmia.

10. The ambulatory medical monitoring and treatment device of claim 9, wherein the at least one processor is further configured to delay an application of the electrical therapy to the patient in response to a determination that CPR is being performed on the patient.

11. The ambulatory medical monitoring and treatment device of claim 1, wherein the at least one processor is further configured to determine a first metric indicative of the general viability of the heart during a first time period, to determine a second metric indicative of the general viability of the heart during a second time period that is subsequent to the first time period, to compare the first metric to the second metric, and to accelerate an application of the therapeutic intervention to the patient in response to the second metric being less than the first metric by a threshold amount.

12. The ambulatory medical monitoring and treatment device of claim 1, wherein the metric is determined for a first period of time, and at least one second period of time that is shorter than the first period of time to determine when the therapeutic intervention is to be applied to the patient.

13. The ambulatory medical monitoring and treatment device of claim 12, wherein the first period of time is approximately four seconds, and each second period of time is approximately 200 milliseconds.

14. The ambulatory medical monitoring and treatment device of claim 13, wherein each second period of time comprises within itself a plurality of successive overlapping windows.

15. The ambulatory medical monitoring and treatment device of claim 14, wherein the at least one processor is further configured to apply the therapeutic intervention to the patient during one of the plurality of successive overlapping windows corresponding to a local maxima of an area of an amplitude spectrum of a ventricular fibrillation waveform.

16. The ambulatory medical monitoring and treatment device of claim 1, wherein the metric is determined over a plurality of intervals of time, and the device is configured to control the therapy delivery interface to apply the defibrillation to the patient at a time corresponding to a local indicia of a sequence of determined values of the metric.

17. The ambulatory medical monitoring and treatment device of claim 16, wherein the plurality of intervals of time are at least one of successive, at least partially overlapping or consecutive.

18. The ambulatory medical monitoring and treatment device of claim 16, wherein the intervals are 100 milliseconds to 1 second in duration.

19. The ambulatory medical monitoring and treatment device of claim 16, wherein the local indicia is based on a first, second or higher order derivative or difference of the sequence of determined values of the metric.

20. The ambulatory medical monitoring and treatment device of claim 16, wherein the at least one processor is configured to determine the local indicia of the sequence of determined values of the metric over a plurality of successive intervals of time and to control the therapy delivery interface to apply the defibrillation to the patient when the most recent determined value of the metric differs from the local indicia by more than a predetermined amount.

21. The ambulatory medical monitoring and treatment device of claim 1, wherein the predetermined timing comprises between approximately 10 seconds and approximately 45 seconds from the onset of the detection of the treatable cardiac arrhythmia.

22. The ambulatory medical monitoring and treatment device of claim 1, wherein modifying the predetermined timing based on the metric comprises shortening the predetermined timing to apply the therapeutic intervention.

23. The ambulatory medical monitoring and treatment device of claim 1, wherein modifying the predetermined timing based on the metric comprises extending the predetermined timing to apply the therapeutic intervention.

24. The ambulatory medical monitoring and treatment device of claim 1, wherein modifying the selection of the therapeutic intervention based on the metric comprises modifying the therapeutic intervention from applying a defibrillating shock to the patient to applying a plurality of pacing pulses to the patient.

25. The ambulatory medical monitoring and treatment device of claim 1, wherein modifying the selection of the therapeutic intervention based on the metric comprises modifying the therapeutic intervention from applying a plurality of pacing pulses to the patient to applying a defibrillating shock to the patient.

26. The ambulatory medical monitoring and treatment device of claim 1, wherein the at least one processor is configured to cause gel to be deployed on to the patient's skin prior to applying the therapeutic intervention.

27. The ambulatory medical monitoring and treatment device of claim 26, wherein the at least one processor is configured to re-calculate the metric after the gel is deployed on to the patient's skin and prior to applying the therapeutic intervention.

* * * * *

UNITED STATES PATENT AND TRADEMARK OFFICE
CERTIFICATE OF CORRECTION

PATENT NO. : 11,324,443 B2
APPLICATION NO. : 15/560598
DATED : May 10, 2022
INVENTOR(S) : Gary A. Freeman and Christopher Luke Kaufman Page 1 of 1

It is certified that error appears in the above-identified patent and that said Letters Patent is hereby corrected as shown below:

On the Title Page

In the References Cited:

Page 2, Column 2, Line 19, Item (56) delete "Quau" and insert --Quan--

Page 2, Column 2, Line 25, Item (56) delete "Quau" and insert --Quan--

Page 2, Column 2, Line 26, Item (56) delete "Quau" and insert --Quan--

Page 3, Column 2, Line 6, Item (56) delete "septum"." and insert --septum",--

In the Drawings

FIG. 3, between reference nos. 330 and 340, delete "Conciousness" and insert --Consciousness--

In the Specification

Column 9, Line 21, delete "(QMM)" and insert --(QWM)--

Column 15, Line 34, delete "and or" and insert --and/or--

Column 20, Line 67, delete "and or" and insert --and/or--

Signed and Sealed this
Sixth Day of September, 2022

Katherine Kelly Vidal
*Director of the United States Patent and Trademark Office*